(12) United States Patent
Connolly et al.

(10) Patent No.: US 10,314,730 B2
(45) Date of Patent: Jun. 11, 2019

(54) FOOT ABDUCTION BRACE

(71) Applicants: Ian Connolly, Newport Beach, CA (US); Jeffrey Yang, LaSalle, CA (US); Francesca Colloredo-Mansfeld, Chapel Hill, NC (US); Brian C. Donnelly, Naperville, IL (US); Robert G. Kopp, Elburn, IL (US); William J. Phillips, Batavia, IL (US); Michael R. Vogler, Oswego, IL (US); Richard Byrne, Marlborough, MA (US); Mark Vasquez, Lancaster, MA (US); Michael Andrew Ahdoot, Encino, CA (US); Kathryn Ann Jaxheimer, San Francisco, CA (US)

(72) Inventors: Ian Connolly, Newport Beach, CA (US); Jeffrey Yang, LaSalle, CA (US); Francesca Colloredo-Mansfeld, Chapel Hill, NC (US); Brian C. Donnelly, Naperville, IL (US); Robert G. Kopp, Elburn, IL (US); William J. Phillips, Batavia, IL (US); Michael R. Vogler, Oswego, IL (US); Richard Byrne, Marlborough, MA (US); Mark Vasquez, Lancaster, MA (US); Michael Andrew Ahdoot, Encino, CA (US); Kathryn Ann Jaxheimer, San Francisco, CA (US)

(73) Assignee: The Board Of Trustees Of The Leland Stanford Junior University, C/O Ms. Katharine Ku, Director Office Of Technology Licensing, Palo Alto, CA (US)

( * ) Notice: Subject to any disclaimer, the term of this patent is extended or adjusted under 35 U.S.C. 154(b) by 954 days.

(21) Appl. No.: 14/488,782

(22) Filed: Sep. 17, 2014

(65) Prior Publication Data
US 2015/0080781 A1 Mar. 19, 2015

Related U.S. Application Data

(60) Provisional application No. 61/878,876, filed on Sep. 17, 2013.

(51) Int. Cl.
*A61F 5/00* (2006.01)
*A61F 5/01* (2006.01)

(52) U.S. Cl.
CPC .................................. *A61F 5/0127* (2013.01)

(58) Field of Classification Search
CPC ...... A61F 5/0111; A61F 5/019; A61F 5/0195; A61F 5/0193; A61F 5/0127;
(Continued)

(56) References Cited

U.S. PATENT DOCUMENTS 3,931,817 A * 1/1976 Infranca ................ A61F 5/0193
602/24
4,088,129 A * 5/1978 DiGiulio ............... A61F 5/0193
602/23
(Continued)

FOREIGN PATENT DOCUMENTS

WO 2010014721 2/2010

OTHER PUBLICATIONS

Fedotov, A., International Search Report and Written Opinion of the International Searching Authority for PCT/US2014/056057, Dec. 25, 2014, pp. 1-6.

*Primary Examiner* — Keri J Nelson
*Assistant Examiner* — Adam Baker
(74) *Attorney, Agent, or Firm* — King & Spalding LLP

(57) ABSTRACT

A foot abduction brace is disclosed herein. The foot abduction brace can include a crossbar having a planar bottom
(Continued)

end. The foot abduction brace can also include a first end disposed on one side of the crossbar. The foot abduction brace can further include a first locking hub removably coupled to the first end in a first position of a plurality of positions, where the first locking hub is disposed in the first keyhole and includes a first coupling feature disposed at a top end of the first locking hub. The foot abduction brace can also include a first footplate having a first complementary coupling feature that removably couples to the first coupling feature of the first locking hub. The foot abduction brace can further include a first foot restraint mechanically coupled to the first footplate.

19 Claims, 13 Drawing Sheets

(58) Field of Classification Search
 CPC ........ A61F 5/0116; A61F 5/0113; A61F 5/14; A61F 5/3715; A61F 5/3753
 USPC ......... 36/140, 142, 143, 144, 160, 161, 158, 36/163, 168; 602/27, 28, 29
 See application file for complete search history.

(56) References Cited

U.S. PATENT DOCUMENTS

| | | | |
|---|---|---|---|
| 4,481,940 A | 11/1984 | Kurtz et al. | |
| 5,470,310 A | 11/1995 | Sutcliffe | |
| 7,267,657 B1 * | 9/2007 | Mitchell | A61F 5/0193 602/23 |
| 7,569,023 B2 | 8/2009 | Dobbs | |
| 7,645,251 B2 | 1/2010 | Hatton et al. | |
| 7,850,631 B2 * | 12/2010 | Mitchell | A61F 5/0193 602/24 |
| 7,867,184 B2 | 1/2011 | Mitchell | |
| 8,075,508 B2 | 12/2011 | Mosler et al. | |

* cited by examiner

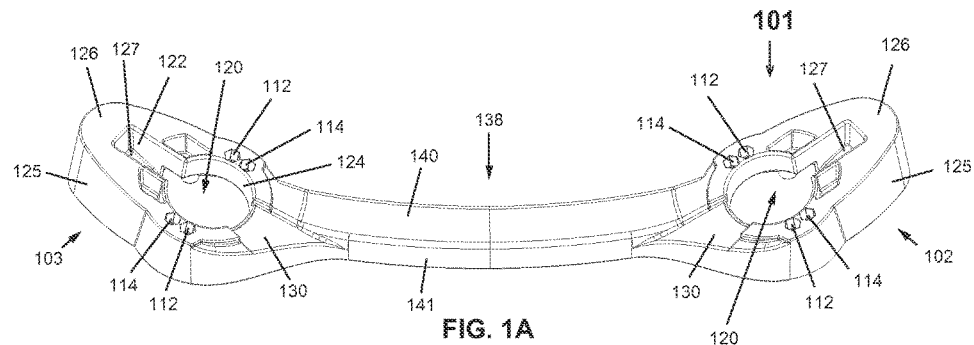
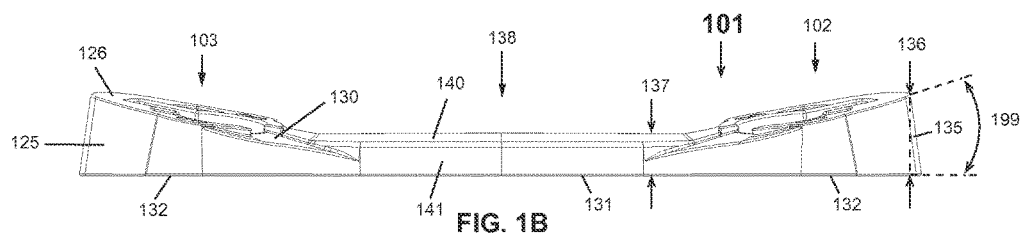
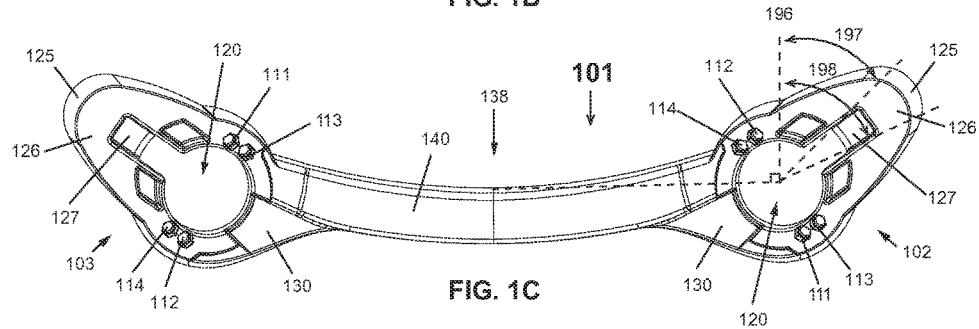
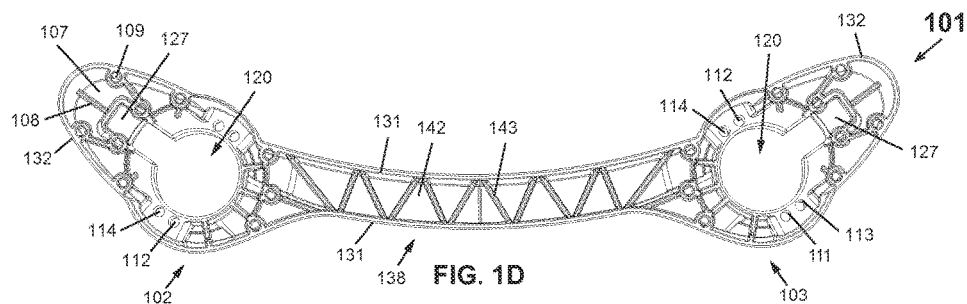

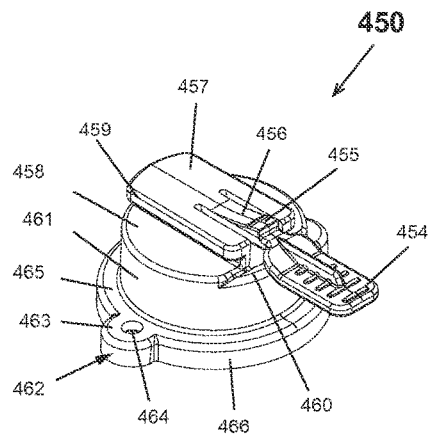
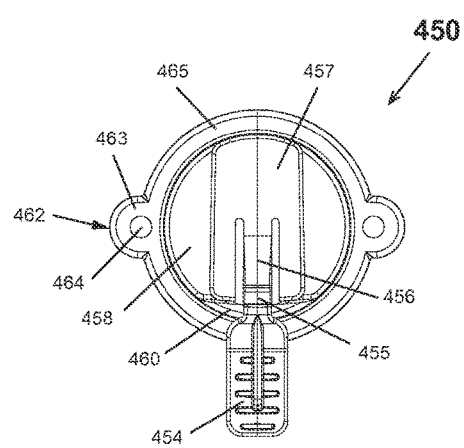
FIG. 4A  FIG. 4B
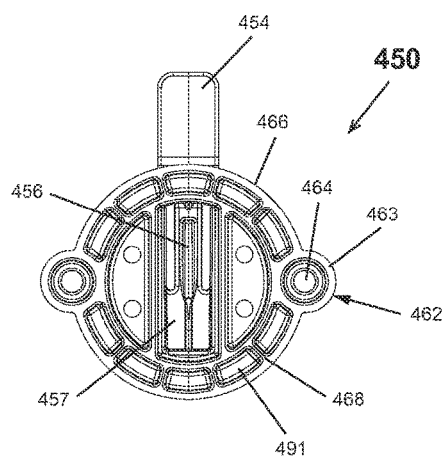
FIG. 4C
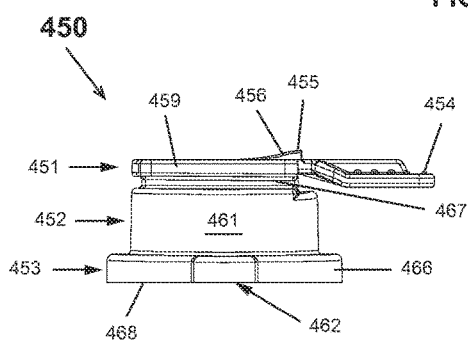
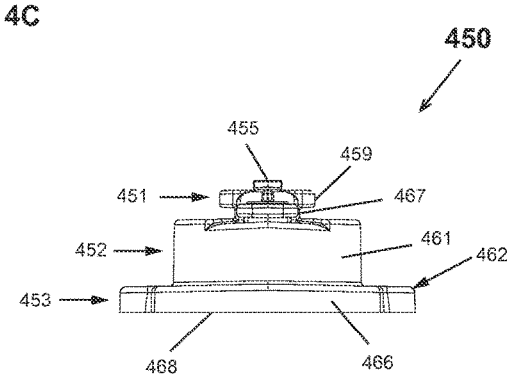
FIG. 4D  FIG. 4E

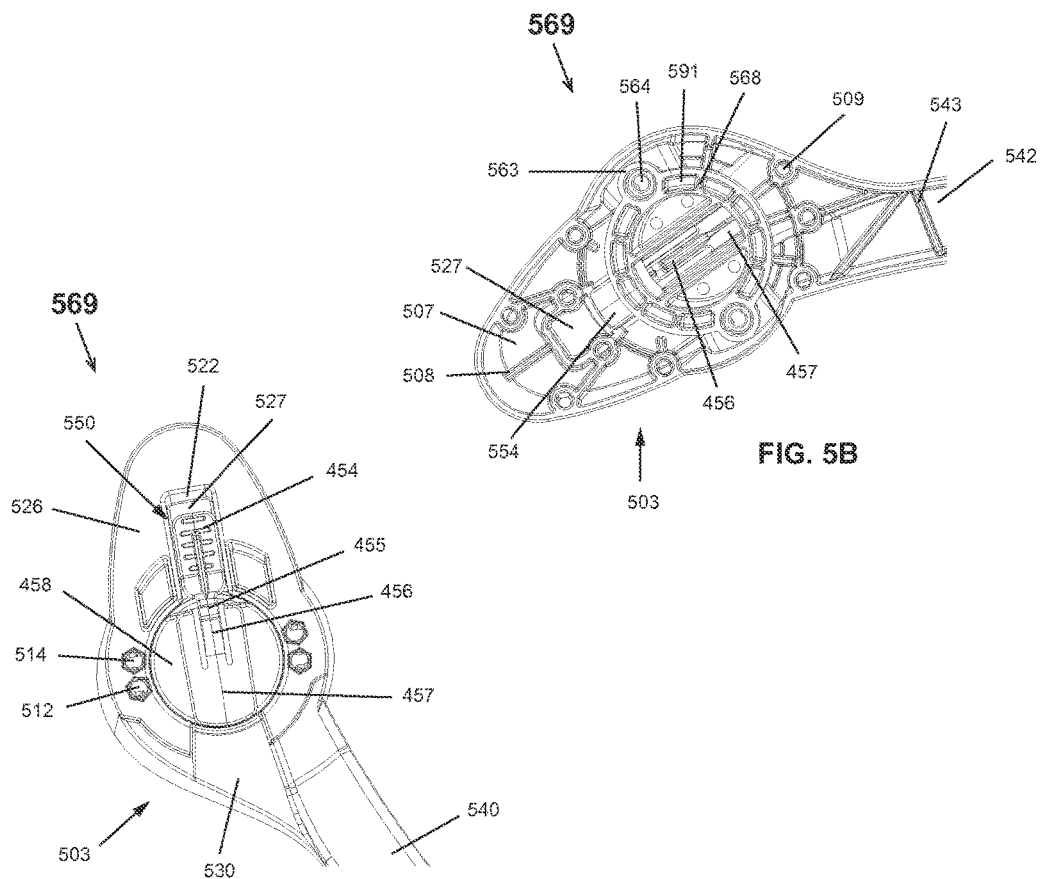
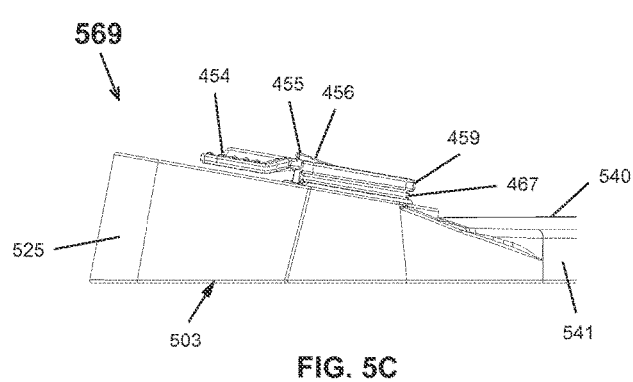

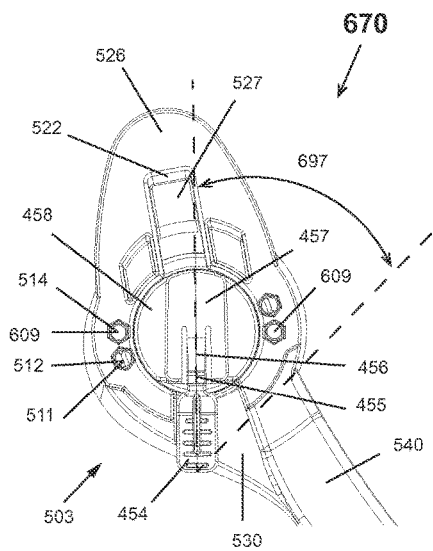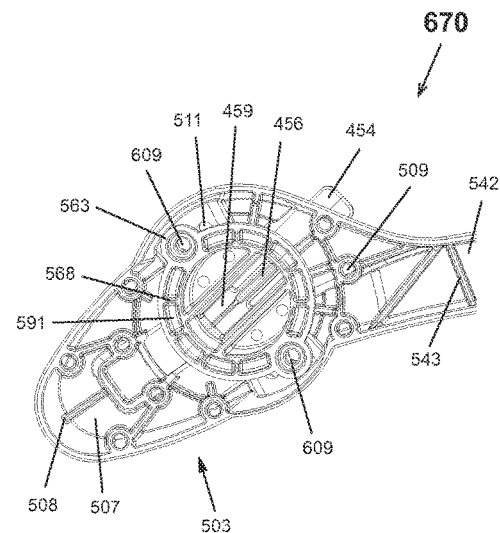
FIG. 6A  FIG. 6B
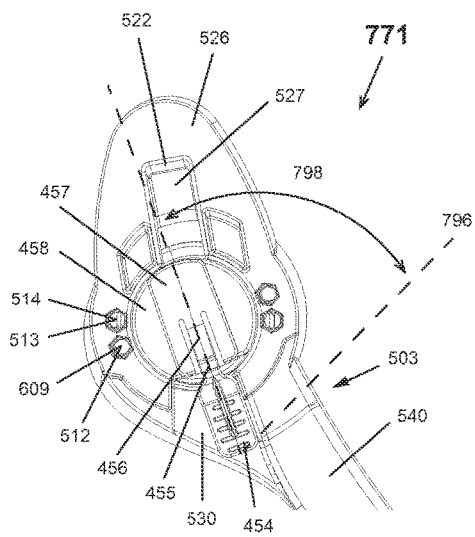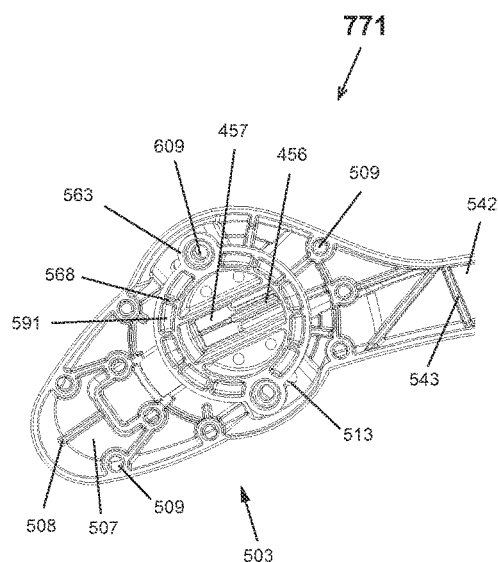
FIG. 7A  FIG. 7B

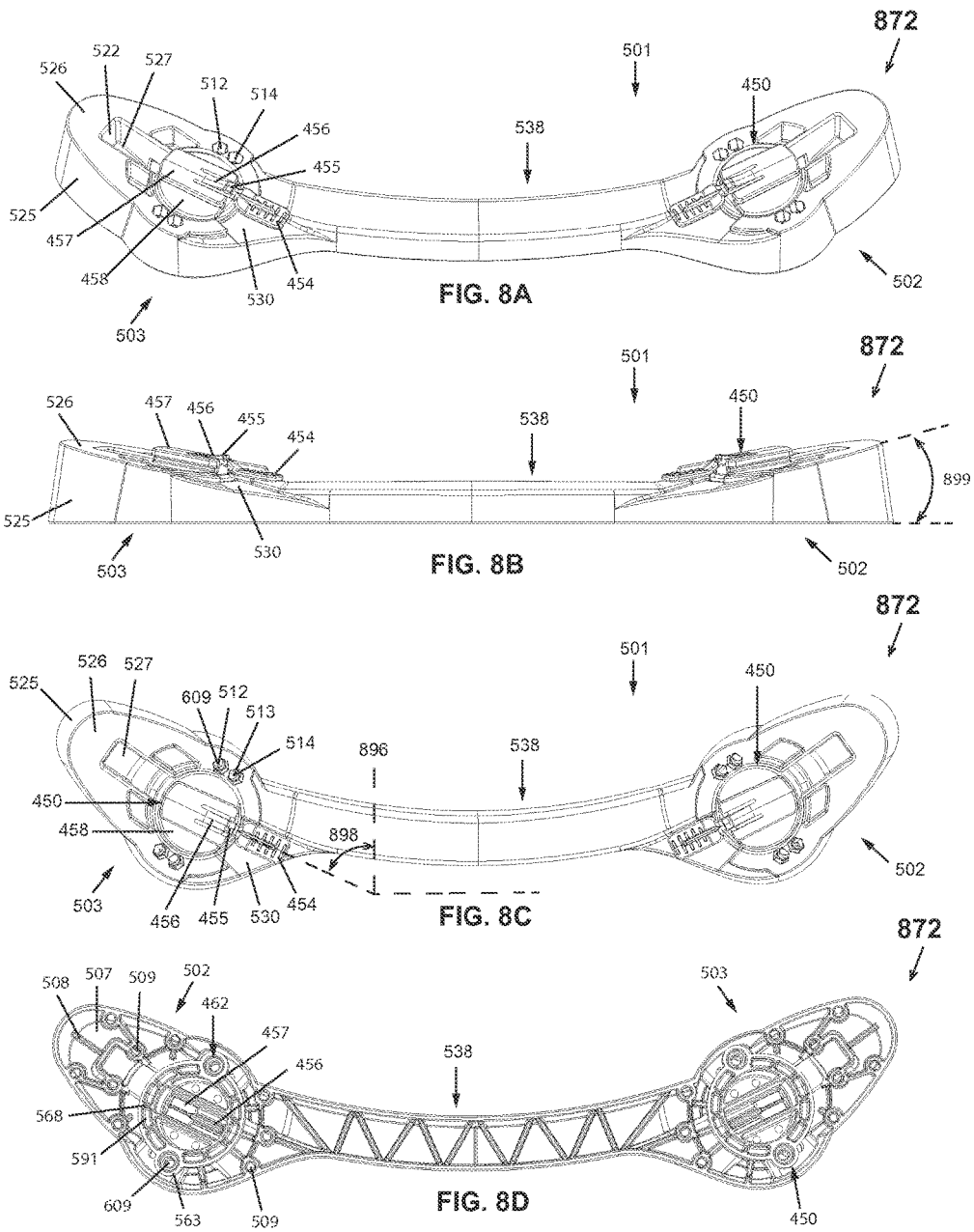

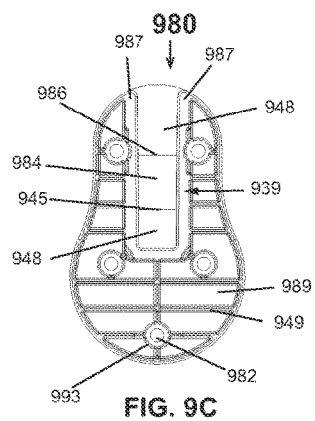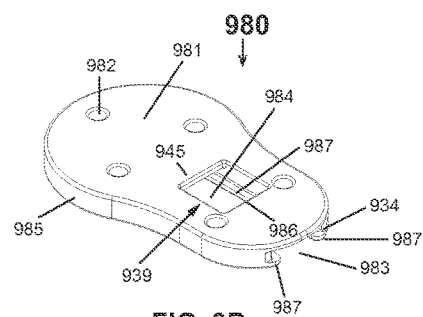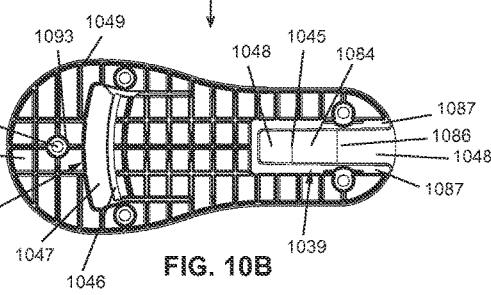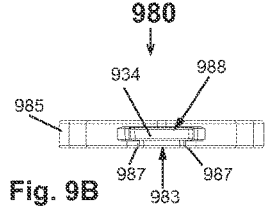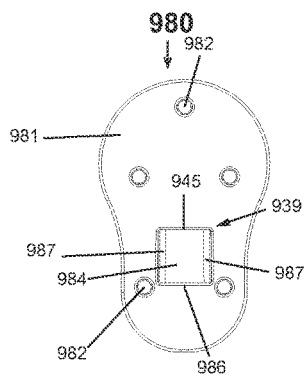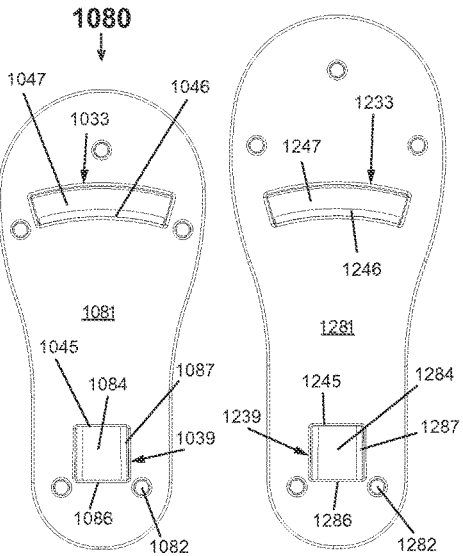

FOOT ABDUCTION BRACE

RELATED APPLICATIONS

The present application claims priority under 35 U.S.C. § 119 to U.S. Provisional Patent Application No. 61/878,876, filed Sep. 17, 2013, and titled "Foot Abduction Brace," the entirety of which is incorporated herein by reference.

TECHNICAL FIELD

Embodiments described herein relate generally to orthopedic braces, and more particularly to systems, methods, and devices for braces to correct clubfoot.

BACKGROUND

Clubfoot, also known as talipes equinovarus, is a congenital birth defect that causes one or both feet to turn inward and/or downward. The exact causes of clubfoot are unknown, but research indicates genetic factors may play a role. Clubfoot results from abnormal development of the muscles, tendons, and bones of the fetus. Shortened tendons and ligaments on the inside of the lower leg lead to the foot turning inward. A tight Achilles tendon contributes to rigidity of the foot.

Clubfoot occurs in approximately 1 out of 750 births, with some variation across countries and ethnic groups and with an increased incidence in children born to a parent with clubfoot. Clubfoot occurs more often in boys than girls. There are about 200,000 new cases of clubfoot each year around the world. For children born with clubfoot, both feet are affected in about 50% of the cases. Without treatment, children born with clubfoot cannot walk properly, if at all, and the untreated condition can lead to severe disability. Treatment can include the use of braces, casts, and/or surgery. Nonsurgical treatment of clubfoot has gained popularity in recent years and consists of a series of leg castings, followed by use of a foot abduction brace for several years.

SUMMARY

In general, in one aspect, the disclosure relates to a foot abduction brace. The foot abduction brace can include a crossbar comprising a planar bottom end. The foot abduction brace can also include a first end disposed on one side of the crossbar, where the first end includes a first keyhole, a top, and the planar bottom end, and where the top of the first end creates a first dorsiflexion angle with the crossbar. The foot abduction brace can further include a first locking hub removably coupled to the first end in a first position of a plurality of positions, where the first locking hub is disposed in the first keyhole and comprises a first coupling feature disposed at a top end of the first locking hub. The foot abduction brace can also include a first footplate that includes a first complementary coupling feature that removably couples to the first coupling feature of the first locking hub. The foot abduction brace can further include a first foot restraint mechanically coupled to the first footplate. The first position can create a first abduction angle between the first foot restraint and a normal position of a foot.

These and other aspects, objects, features, and embodiments will be apparent from the following description and the appended claims.

BRIEF DESCRIPTION OF THE DRAWINGS

The drawings illustrate only example embodiments of foot abduction braces and are therefore not to be considered limiting of its scope, as foot abduction braces may admit to other equally effective embodiments. The elements and features shown in the drawings are not necessarily to scale, emphasis instead being placed upon clearly illustrating the principles of the example embodiments. Additionally, certain dimensions or positionings may be exaggerated to help visually convey such principles. In the drawings, reference numerals designate like or corresponding, but not necessarily identical, elements.

FIGS. 1A-1D show various views of a crossbar of an example foot abduction brace in accordance with certain example embodiments.

FIGS. 4A-4E show various views of a locking hub in accordance with certain example embodiments.

FIGS. 5A-5C show various views of a subassembly of a locking hub and a portion of a crossbar in accordance with certain example embodiments.

FIGS. 6A and 6B show various views of the subassembly of FIGS. 5A-5C where the locking hub forms a first abduction angle in accordance with certain example embodiments.

FIGS. 7A and 7B show various views of the subassembly of FIGS. 5A-5C where the locking hub forms a second abduction angle in accordance with certain example embodiments.

FIGS. 8A-8D show various views of another subassembly of the crossbar and locking hubs from FIGS. 7A and 7B in accordance with certain example embodiments.

FIGS. 9A-9D show various views of a footplate in accordance with certain example embodiments.

FIGS. 10A and 10B show various views of another footplate in accordance with certain example embodiments.

FIGS. 11 and 12 show top views of other foot plates in accordance with certain example embodiments.

DETAILED DESCRIPTION OF EXAMPLE EMBODIMENTS

Figure 2A:
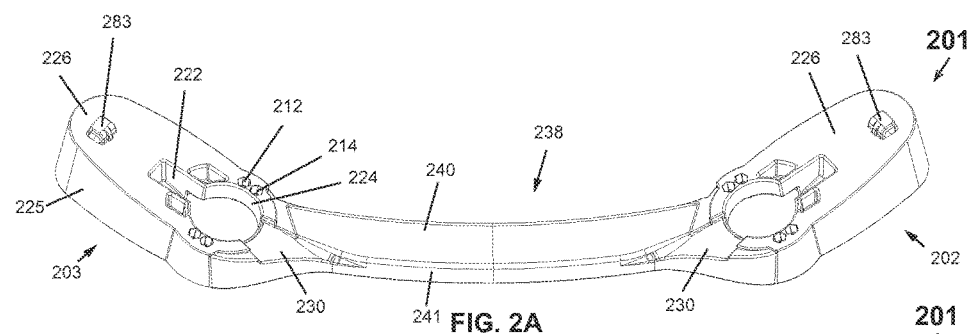
FIGS. 2A-2D show various views of another crossbar of an example foot abduction brace in accordance with certain example embodiments.

The example embodiments discussed herein are directed to systems, apparatuses, and methods of foot abduction braces. While the example foot abduction braces shown in the Figures and described herein are directed to correction of a clubfoot condition, example foot abduction braces can be used in the treatment of other deformities and/or conditions, whether of the foot and/or leg. Thus, the examples of foot abduction braces described herein are not limited to use in the treatment of clubfoot.

When an infant is born with clubfoot, one or both feet are turned inward and downward relative to a "normal" position of the feet. A number of methods (including the Ponseti method) are used to treat clubfoot. These methods involve positioning the affected feet in an outward and upward position (relative to a "normal" position of the feet) for amounts of time over an extended period, this outward and upward position is exaggerated in an effort to correct the clubfoot so that the feet align and grow in a "normal" position. The outward position of the foot from "normal" is called an abduction angle, which represents the outward angle from "normal" that the foot is positioned. The upward position of the foot from "normal" is called the dorsiflexion angle, which represents the upward angle from "normal" that the foot is positioned. Example embodiments allow the feet affected by clubfoot or similar condition to be positioned at both an abduction angle and a dorsiflexion angle. One or both of these angles can be adjusted in the field (e.g., by a doctor in a doctor's office, by a parent at home) in example embodiments.

A coupling feature (including a complementary coupling feature) as described herein can allow one or more components and/or portions of an indicator light (e.g., a housing) to become mechanically and/or electrically coupled, directly or indirectly, to another portion (e.g., a guard) of the indicator light and/or to an electrical enclosure. A coupling feature can include, but is not limited to, portion of a hinge, an aperture, a recessed area, a protrusion, a slot, a spring clip, a tab, a detent, and mating threads. One portion of an example indicator light can be coupled to another portion of an indicator light and/or to an electrical enclosure by the direct use of one or more coupling features.

The foot abduction braces described herein may be used with feet of any size and/or shape. For example, example embodiments of foot abduction braces can be used with newborn infants, adolescents, or teenaged children. Further, an example embodiment used to secure one foot to a foot restraint of a brace can be the same or a different example embodiment used to secure the other foot to the other foot restraint of the brace. As defined herein, a user can be any person that wears, adjusts, or prescribes an example foot abduction brace. Examples of a user can include, but are not limited to, an infant with clubfoot (or other foot or leg deformity), a child with clubfoot (or other foot or leg deformity), a parent of an infant or child with clubfoot (or other foot or leg deformity), a doctor, a doctor's assistant, a physiotherapist, a nurse, a volunteer, and a company representative.

The various components of the example foot abduction braces described herein can be made from one or more of a number of materials. Such materials can include, but are not limited to, plastic, rubber, metal, and wood. A number of the concepts behind example foot abduction braces includes having a brace that is easy for a doctor (or other similar user) to assemble and set a brace that is relatively inexpensive to manufacture. The example brace can be durable and effective for treating a foot abduction. Example embodiments can be configured so that the person wearing the brace is not easily adjusted without the proper tools. The example embodiments can be relatively lightweight. The example foot abduction braces can allow a user to stand and move while wearing the brace.

Any component described in one or more figures below can apply to a corresponding component having a similar label in one or more other figures. In other words, the description for any component of a figure can be considered substantially the same as the corresponding component described with respect to another figure. Further, if a component is described but not expressly shown or labeled in a figure, that component and/or its description can be inferred from a corresponding component of another figure. Conversely, if a component in a figure is labeled but not described, the description for such component can be substantially the same as the description for the corresponding component with respect to another figure. The numbering scheme for the components in a figure herein parallels the numbering scheme for the components of other figures in that each component is a three digit number having the identical last two digits.

Example embodiments of foot abduction braces will be described more fully hereinafter with reference to the accompanying drawings, in which example embodiments of foot abduction braces are shown. Foot abduction braces may, however, be embodied in many different forms and should not be construed as limited to the example embodiments set forth herein. Rather, these example embodiments are provided so that this disclosure will be thorough and complete, and will fully convey the scope of foot abduction braces to those of ordinary skill in the art. Like, but not necessarily the same, elements (also sometimes called modules) in the various figures are denoted by like reference numerals for consistency.

Terms such as (but not limited to) "first," "second," "end," "left," "right," "top," "bottom," "side," "distal," and "proximal" are used merely to distinguish one component (or part of a component or state of a component) from another. Such terms are not meant to denote a preference or a particular orientation. Also, the names given to various components described herein are descriptive of one embodiments and are not meant to be limiting in any way. Those of ordinary skill in the art will appreciate that a feature and/or component shown and/or described in one embodiment (e.g., in a figure) herein can be used in another embodiment (e.g., in any other figure) herein, even if not expressly shown and/or described in such other embodiment.

In one or more embodiments, one or more of the components shown in any of the following figures may be omitted, repeated, and/or substituted. Accordingly, embodiments of the various components of the foot abduction brace should not be considered limited to the specific arrangements of components shown in a particular figure.

FIGS. 1A-1D show various views of a crossbar 101 of an example foot abduction brace in accordance with certain example embodiments. Specifically, FIG. 1A shows a top-side perspective view of an example crossbar 101. FIG. 1B shows a side view of the crossbar 101. FIG. 1C shows a top view of the crossbar 101. FIG. 1D shows a bottom view of the crossbar 101.

Referring to FIG. 1A-1D, the crossbar 101 includes a central portion 138 and a left end segment 102, and a right end segment 103. The left end segment 103 is disposed at one end segment of the central portion 138, and the right end segment 102 is disposed at the other, opposite end segment of the central portion 138. The central portion 138, the right end segment 102, and the left end segment 103 can be made from a single piece, as from a mold. Alternatively, the central portion 138, the right end segment 102, and the left end segment 103 can be separate pieces that are coupled to each other, directly or indirectly, using one or more of a number of coupling methods, including but not limited to welding, fusion, epoxy, compression fittings, coupling devices (e.g., screws, nuts, bolts, rivets), slots, tabs, and detents.

In certain example embodiments, the central portion 138 includes a top 140, a back side 141, a bottom side 142 having a number of reinforcements 143, and a bottom border 131. One or more of the reinforcements 143 can extend to a point that is planar with the bottom border 131, so that such reinforcements 143 can contact a flat surface along with the bottom border 131 when the crossbar 101 is placed on such flat surface. Alternatively, one or more of the reinforcements 143 can extend to a point that is short of the bottom border 131, so that such reinforcements 143 do not contact a flat surface along with the bottom border 131 when the crossbar 101 is placed on such flat surface.

The central portion 138 can be substantially planar. In addition, or in the alternative, the central portion 138 can have some curvature or other variation when viewed from atop (as shown in FIG. 1C), the front, and/or the back. In addition, or in the alternative, the plane defined by the bottom border 131 can be parallel to, or antiparallel with, the plane defined by the top 140. For example, as shown in FIG. 1B, the plane defined by the top 140 slopes from front to back, while the plane defined by the bottom border 131 is flat, making the two planes antiparallel relative to each other. Any curvature in the vertical cross section can contribute, at least in part, to an angle of dorsiflexion. For example, the crossbar 101 can be shaped to create a 10° angle of dorsiflexion. As explained below, based on an amount of flex in the central portion 108 between the left end segment 103 and the right end segment 102, the angle of dorsiflexion in the crossbar 101 can remain substantially constant when a user attempts to stand and/or walk while the user's feet are engaged with the foot restraints of the brace.

In addition, or in the alternative, the central portion 138 can, in the horizontal cross section, be straight, convexly curved, concavely curved, or have some other shape. The length of the central portion 138 can be fixed or adjustable. The length of the central portion 138 can be suitable for a user (for example, person wearing the foot abduction brace) of a certain size to effectively use the foot abduction brace to correct the effects of clubfoot or some other deformity. For example, the length of the central portion 138 (with or without the right end segment 102 and the left end segment 103) can be approximately 18 centimeters (cm). As another example, the length of the central portion 138 (with or without the right end segment 102 and the left end segment 103) can be approximately 30 centimeters (cm). As yet another example, the length of the central portion 138 (with or without the right end segment 102 and the left end segment 103) can be approximately 22 centimeters (cm). Other lengths can include, but are not limited to, 26 cm and 36 cm.

In certain example embodiments, one or both ends (the right end segment 102, the left end segment 103) includes a top 126, a side 125 that wraps around at least a majority of the respective end, a bottom side 107 having a number of reinforcements 108, and a bottom border 132. One or more of the reinforcements 108 can extend to a point that is planar with the bottom border 132, so that such reinforcements 108 can contact a flat surface along with the bottom border 132 when the respective end is placed on such flat surface. Alternatively, one or more of the reinforcements 108 can extend to a point that is short of the bottom border 132, so that such reinforcements 108 do not contact a flat surface along with the bottom border 132 when the respective end is placed on such flat surface. The bottom border 132 of each end (the right end segment 102, the left end segment 103) can be substantially planar with the bottom border 131 of the central portion 138.

Adjacent to one or more of the reinforcements 108 can be disposed one or more standoffs 109. In such a case, the standoffs 109 can have an aperture into which a "foot" can be inserted. The length of the standoff 109, when housing a "foot", can be substantially the same as the length of the bottom border 132. Such a "foot" can be made of one or more suitable materials (e.g., rubber, plastic) and can be used to help stabilize the brace when a user is standing and/or "walking" while wearing the example brace.

In certain example embodiments, the height of the side 125 can vary around the respective end. For example, as shown in FIGS. 1A-1C, the height of the side 125 for both the right end segment 102 and the left end segment 103 is greatest at the distal end segment of the respective end (where height 135 is located, having a vertical height 136). Further, the height of the side 125 gradually decreases until the height of the side 125 at the proximal end (i.e., where the respective end meets the central portion 138) is substantially equal to the vertical height 137 of the central portion 138. In such a configuration, the end can promote a dorsiflexion angle 199. The dorsiflexion angle places the foot disposed in the foot restraint coupled to the end (explained below) in a position that opposes the position of a clubfoot (in an effort to correct the clubfoot condition according to a prevailing method such as the Ponseti method). In this example, the dorsiflexion angle is approximately 10°.

One or both ends (right end segment 102, left end segment 103) of the crossbar 101 can have one or more features. For example, as described above, a keyhole 120 can be disposed at one or both ends (right end segment 102, left end segment 103). In this example, there is a keyhole 120 at both the right end segment 102 and at the left end segment 103. The keyholes 120 and other features of the right end segment 102 and the left end segment 103 are symmetrical to each other. Each keyhole 120 includes a core section 124 that is substantially circular and substantially traverses the entire thickness 125 of the right end segment 102 and the left end segment 103. Each keyhole 120 can also have one or more other features. For example, as shown in FIGS. 1A-1D, each keyhole 120 can have an extended section 122 that extends from one side of the core section 124 of the keyhole 120. The extended section 122 can be substantially rectangular and can also substantially traverse the entire thickness 125 of the right end segment 102 and the left end segment 103.

In certain example embodiments, a lip 127 can be disposed in some or all of the extended section 122. The lip 127 can be disposed at a distal end or a proximal end segment of the extended section 122. For example, in this case, the lip 127 can extend approximately halfway into the extended section from the distal end. The lip 127 can be disposed at some location between the top surface 126 of the respective end (e.g., the right end segment 102, the left end segment 103) and the distal end segment of the extensions 108 of such respective end.

Another example feature of one or both ends of the crossbar 101 can be a recessed area 130. Each recessed area 130 can have a thickness that is less than the thickness of the adjacent portions of the right end segment 102 and the left end segment 103. In addition, the thickness of the recessed area 130 can be less than the height of the side 125 adjacent to the recessed area 130. The recessed area 130 can have a fixed or variable width. Each recessed area 130 can extend from a portion of the keyhole 120 (in this case, from a portion of the core section 124 of the keyhole 120) to an outer edge of the respective end. The recessed area 130 can be used to limit the range of movement of the tab 454 of the locking hub 450, as explained below with respect to FIGS.

4A-4E. In certain example embodiments, the recessed area 130 is positioned adjacent to the core section 124 of the keyhole 120 and substantially opposite the extended section 122 of the keyhole 120. Alternatively, the extended section 122 of the keyhole 120 can be positioned at any other location around the core section 124 of the keyhole 120 relative to the recessed area 130. For example, the extended section 122 of the keyhole 120 can be positioned within the recessed area 130.

Yet another feature of one or both ends of the crossbar 101 can be one or more coupling features, in this case called abduction angle features (e.g., abduction angle feature 111, abduction angle feature 113). There can be one or more sets of abduction angle features. For example, the right end segment 102 and the left end segment 103 of FIGS. 1A-1D can each have two sets of abduction angle features, where each set has two abduction angle features 111 and 113. The abduction angle features 111 and 113 can traverse some or all of the height of the right end segment 102 and the left end segment 103. Each abduction angle feature 111 and 113 can have substantially the same size and/or features as each other. The abduction angle features can allow the foot of a person afflicted with clubfoot to be positioned at a particular abduction angle. For example, abduction angle features 111 allow the foot to be placed at abduction angle 198 (approximately 65° from a "normal" position 196 of the foot), and abduction angle features 113 allow the foot to be placed at abduction angle 197 (approximately 45° from a "normal" position 196 of the foot).

The size and/or features of each abduction angle feature 111 and 113 can be substantially the same or vary along its length. For example, the abduction angle features 111 and 113 in FIGS. 1A-1D can have the shape of a hexagon (as to fit a nut) at the top end, a narrower cylinder (as to fit a screw or bolt) at the lower end, and/or mating threads disposed on the walls therebetween. In certain example embodiments, one or more abduction angle features (e.g., abduction angle feature 111, abduction angle feature 113) can be reinforced with a coupling feature (e.g., coupling feature 112, coupling feature 114). For example, as shown in FIGS. 1A-1D, the coupling feature 112 of each abduction angle feature 111 can be a threaded sleeve, and the coupling feature 114 of each abduction angle feature 113 can be a threaded sleeve. The coupling features 112, 114 can be made of the same material as, or a different material than, the rest of the crossbar 101. For example, the coupling features 112, 114 can be made of metal, and the rest of the crossbar 101 can be made of plastic.

Some or all of the crossbar 101 can be solid or have other features along its thickness. For example, as can be seen in FIGS. 1A-1D, the top side various portions (e.g., the top 140 of the central portion 138, the top 126 of the right end segment 102 and the left end segment 103) of the crossbar 101 can be relatively smooth and solid, while a number of reinforcements (e.g., reinforcements 143, reinforcements 108) can extend downward from the top (e.g., reinforcements 143 extending downward from the top 140 of the central portion 138, reinforcements 108 extending downward from the top 126 of the right end segment 102 and the left end segment 103). In certain example embodiments, the various reinforcements have a shape, size, and orientation that control the rigidity, stiffness, and durability of the crossbar 101 so that the crossbar 101 can withstand the various forces applied by a user wearing the example brace.

Figure 2B:
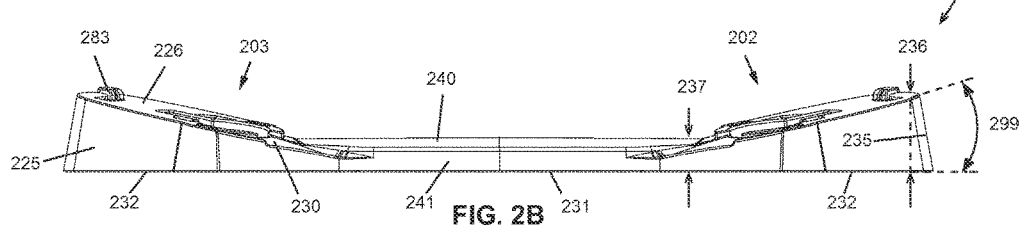
Figure 2C:
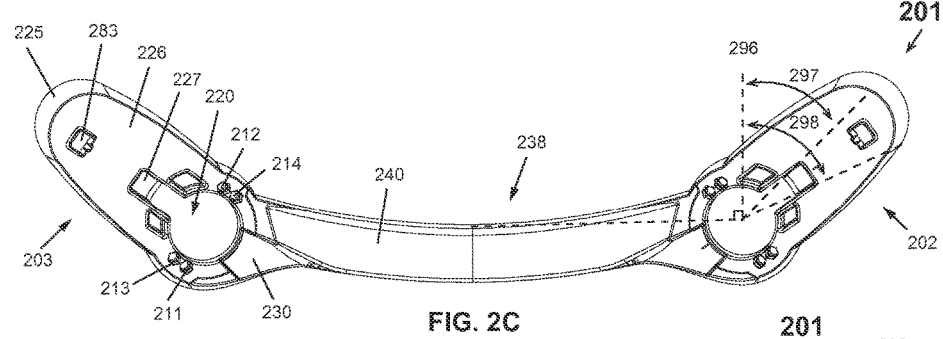
Figure 2D:
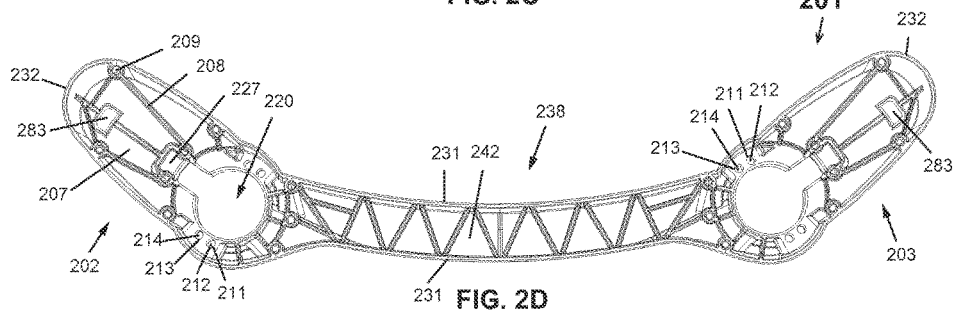

FIGS. 2A-2D show various views of another crossbar of an example foot abduction brace in accordance with certain example embodiments. Specifically, FIG. 2A shows a top-side perspective view of an example crossbar 201. FIG. 2B shows a side view of the crossbar 201. FIG. 2C shows a top view of the crossbar 201. FIG. 2D shows a bottom view of the crossbar 201. Referring to FIGS. 1A-2D, the crossbar 201 of FIGS. 2A-2D is substantially the same as the crossbar 101 of FIGS. 1A-1D, except as described below.

The ends (right end segment 202, left end segment 203) of the crossbar 201 of FIGS. 2A-2D are longer that the ends (right end segment 102, left end segment 103) of the crossbar 101 of FIGS. 1A-1D. In such a case, the size, shape, and dimensions of the keyhole 202 can be substantially the same as the size, shape, and dimensions of the keyhole 102. This allows the same locking hub 450 (described below with respect to FIGS. 4A-4E) to be used with a number of crossbars of varying sizes, which can accommodate users of varying size (e.g., height, weight, foot size). In addition, or in the alternative, the number, configuration, and position of the abduction angle features (e.g., abduction angle feature 211, abduction angle feature 213) in FIGS. 2A-2D can be substantially the same as the number, configuration, and position of the corresponding abduction angle features of FIGS. 1A-1D.

When the ends (e.g., right end segment 202, left end segment 203) reach a certain length, additional features, not found with the ends having a shorter length (e.g., right end segment 102, left end segment 103) can be included with the respective end. For example, as shown in FIGS. 2A-2D, the right end segment 202 and the left end segment 203 can have a coupling feature 283 that protrudes outward from the top 226 of each respective end. The coupling feature 283 can be used to couple to a complementary coupling feature of the footplate, as described below with respect to FIGS. 10A-12. The coupling feature 283 can form a single piece with the respective end (e.g., right end segment 202, left end segment 203), as from a mold. Alternatively, the coupling feature 283 can be a separate piece that is coupled to the respective end using one or more of a number of coupling methods, including but not limited to welding, fusion, epoxy, compression fittings, coupling devices (e.g., screws, nuts, bolts, rivets), slots, tabs, and detents.

The shape, size, location, and configuration of such coupling features 283 can vary. For example, as in this case, each coupling feature 283 can be a tab located toward the distal end segment of the respective end, where the tab initially extends away (upward) from the top 226 of the respective end, and then extends outward toward the distal end segment of the respective end. Such a coupling feature 283 can be used when the footplate is large, allowing for additional support to secure a larger sized foot to the brace. As discussed above, the ends (in this case, right end segment 202, left end segment 203) in FIGS. 2A-2D are longer than the length of the ends in FIGS. 1A-1D. In addition, or in the alternative, the length of the central portion 238 in FIGS. 2A-2D can be longer than the length of the central portion 138 in FIGS. 1A-1D.

Figure 3A:
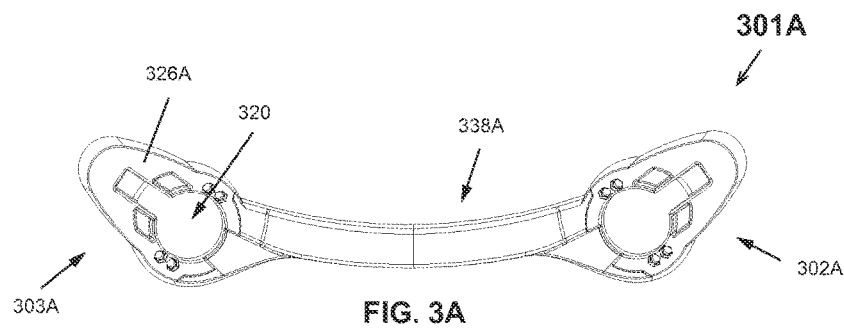
FIGS. 3A-3C show top views of a number of crossbars of example foot abduction braces in accordance with certain example embodiments.
Figure 3B:
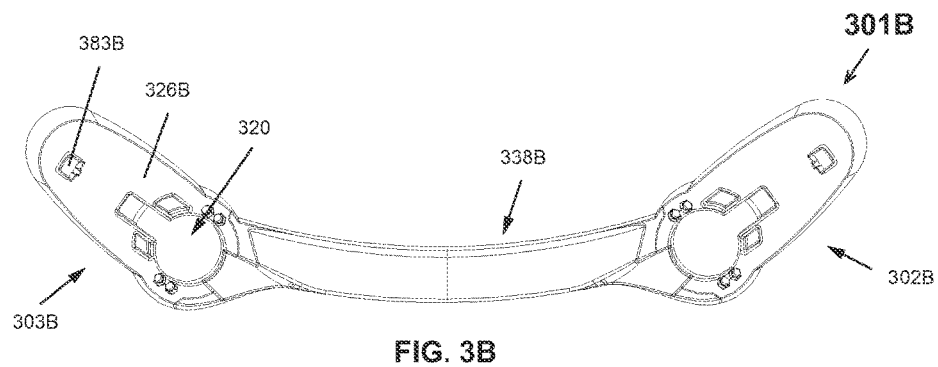
Figure 3C:
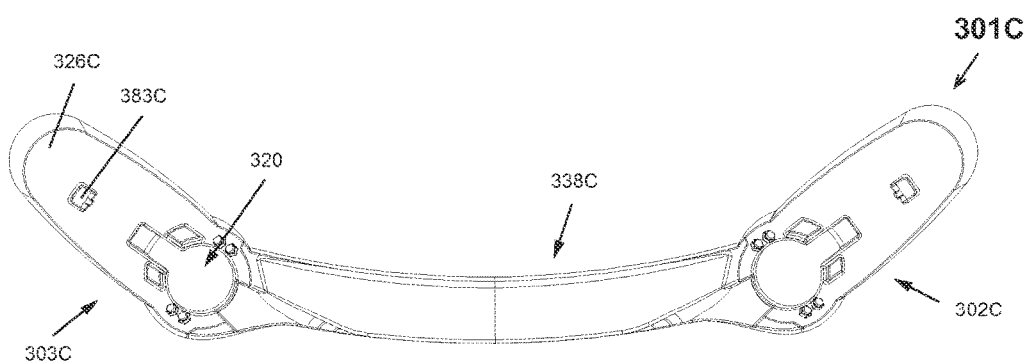

FIGS. 3A-3C show top views of three crossbars 301 in accordance with certain example embodiments. Aside from the size of the ends and the central portion, the crossbars of FIGS. 3A-3C are substantially the same as the crossbar 101 of FIGS. 1A-1D and the crossbar 201 of FIGS. 2A-2D. For the crossbar 301A of FIG. 3A, the right end segment 302A and the left end segment 303A are substantially the same as each other and are disposed on opposite ends of the central portion 338A. Similarly, for the crossbar 301B of FIG. 3B, the right end segment 302B and the left end segment 303B are substantially the same as each other and are disposed on opposite ends of the central portion 338B. Finally, for the crossbar 301C of FIG. 3C, the right end segment 302C and the left end segment 303C are substantially the same as each other and are disposed on opposite ends of the central portion 338C.

As noted above, as shown in FIGS. 3A-3C, the size (e.g., the length of the central portion 338) can vary from crossbar to crossbar. As the length of the central portion 338 (or other measure of size of the crossbar) increases, the length of each end (e.g., right end segment 302, left end segment 303) can also increase. Specifically, while the shape and size of the keyhole 320 can remain substantially the same for any size of the central portion 338 and/or an end, the end can extend further away from the keyhole 320. Again, for larger ends, one or more coupling features 383 (e.g., coupling features 383B in FIG. 3B, coupling features 383C in FIG. 3C) can be disposed toward the distal end on the respective end. In this case, the coupling features 383B are disposed on the top 326B of each respective end segment of the crossbar 301B, and the coupling features 383C are disposed on the top 326C of each respective end segment of the crossbar 301C. Since the ends of the crossbar 301A are relatively small, there are no coupling features disposed on the top 326A of those ends.

FIGS. 4A-4E show various views of a locking hub 450 in accordance with certain example embodiments. Specifically, FIG. 4A shows a top/perspective view of the locking hub 450. FIG. 4B shows a top view of the locking hub 450. FIG. 4C shows a bottom view of the locking hub 450. FIG. 4D shows a side view of the locking hub 450. FIG. 4E shows a front view of the locking hub 450.

Referring to FIGS. 1A-4E, the locking hub 450 of FIGS. 4A-4E can include a coupling feature 451, a base 453, and an intermediate section 452. In certain example embodiments, the coupling feature 451 includes one or more mechanisms that mechanically couple (or decouple) the locking hub 450 with a footplate (described below with respect to FIGS. 9A-12) of the example foot abduction brace. For example, as shown in FIGS. 4A-4E, the coupling feature 451 can include a slotted tongue 457, a stop 455 that is connected to a slotted tongue 457 by a ramp 456, and a tab 454 that is mechanically coupled to the stop 455.

The slotted tongue 457 can have a shape and size that allows the locking hub 450 to moveably (e.g., slidably) couple to a footplate. For example, as shown in FIGS. 4A-4E, the slotted tongue 457 can have an outer side 459 and can be mounted on a base 467, where the outer side 459 extends outward (laterally) beyond the base 467 at the front and both sides. In other words, when viewed from above, the base 467 cannot be seen because the outer sides 459 of the slotted tongue 457 extend laterally beyond the base 467. The ramp 456 can be coupled to the slotted tongue 457 in such a way that the stop 455 and the ramp 456 are able to move in a vertical direction relative to and independently of the slotted tongue 457. This allows the stop 455 to slide into a certain position relative to a footplate and mechanically couple to a corresponding receiving feature 414 of a footplate. The tab 454 can be depressed to move the stop 455 and at least the adjacent part of the ramp 456 vertically downward, which releases the stop 455 from a complementary coupling feature of a footplate, allowing the footplate to decouple (e.g., slide) from the locking hub 450 using the slotted tongue 457. In other words, by pressing the tab 454, a footplate can decouple from the coupling feature 451 of the locking hub 450 in reverse of how the footplate couples to the coupling feature 451 of the locking hub 450.

The shape and size of the tab 454 can be such that the tab 454 can fit within the extended section (e.g., extended section 122) of the keyhole (e.g., keyhole 120) of a an end (e.g., right end segment 102, left end segment 103) of a crossbar (e.g., crossbar 101). Specifically, as shown below with respect to FIGS. 5A-5C, the shape and size of the tab 454 can allow the tab 454 to traverse the extended section of a keyhole. In certain example embodiments, the intermediate section 452 of the locking hub 450 is positioned between, and is mechanically coupled to, the base 453 and the coupling feature 451. Specifically, the coupling feature 451 can be disposed atop the intermediate section 452, and the base 453 can be disposed below the intermediate section 452.

The coupling feature 451, the intermediate section 452, and/or the base 453 can be formed from a single piece (as from a mold). Alternatively, the coupling feature 451, the intermediate section 452, and/or the base 453 can be discrete pieces that are mechanically coupled to each other using one or more of a number of coupling methods, including but not limited to epoxy, welding, compression fittings, slots, tabs, detents, and coupling devices (e.g., bolts, nuts). The intermediate section 452 can be shaped substantially the same as a core section (e.g., core section 124) of a keyhole (e.g., keyhole 120) and can be disposed within the core section of the keyhole when the coupling feature 451 of the locking hub 450 is mechanically coupled to a footplate. Further, the size of the intermediate section 452 can be less than (e.g., slightly less than, substantially less than) the size of the core section of the keyhole.

In addition, as discussed below with respect to FIGS. 5A-5C, the intermediate section 452 can rotate while disposed within the core section of a keyhole. In such a case, the shape of the intermediate section 452 and the shape of the core section of the keyhole can be substantially round when viewed from above. Further, in order for the coupling feature 451 to fit through the keyhole to allow the intermediate section 452 to be disposed within the keyhole, the slotted tongue 457, the ramp 456, and the stop 455 can be contained within the vertical extension of the intermediate section 452. For example, when viewed from above (as shown in FIG. 4C), the slotted tongue 457, the ramp 456, and the stop 455 do not extend laterally beyond (when viewed from above) the outer edge (as denoted by side wall 461) of the intermediate section 452.

On the other hand, because of the extended section of the keyhole, as well as the shape and size of the extended section, the tab 454 of the coupling feature 451 can extend laterally beyond (when viewed from above) the vertical extension of the intermediate section 452. When the locking hub 450 is properly positioned within the keyhole, such that the intermediate section 452 is positioned within the central portion (e.g., central portion 124) of the keyhole, the coupling feature 451 is positioned above the keyhole, which allows the coupling feature 451 to mechanically couple to the footplate.

The base 453 of the locking hub 450 can have a size (when viewed from above) that is larger than the size of the intermediate section 452. Thus, when the intermediate section 452 is disposed within the central portion of a keyhole, the top surface 465 of the base 453 can abut against the bottom side of the end (e.g., right end segment 102, left end segment 103) of the crossbar and prevent the locking hub 450 from traversing further upward through the keyhole, as can be seen below with respect to FIGS. 5A-5C. The base 453 can have a thickness around its perimeter (as shown by side wall 466) that can vary.

In certain example embodiments, the base 453 includes one or more of a number of coupling features 462. The coupling features 462 can be used to couple, directly or indirectly, the locking hub 450 with one or more other components of an example brace. In this example, the coupling features 462 can be used to couple the locking hub 450 to an end (e.g., right end segment 102, left end segment 103) of a crossbar (e.g., crossbar 101) to set an abduction angle. In this example, there are two substantially identical coupling features 462, where each coupling feature 462 includes an extension 463 disposed on opposite sides of the base 453 from each other and extending outward from the side wall 466 of the base 453. Each of the extensions 463 can have a height that is substantially similar to the height of the side wall 466. Each coupling feature 462 in this case also includes an aperture 464 that traverses the entire height of the extension 463.

In certain example embodiments, each coupling feature 462 (also called an abduction angle feature 462) of the base 453 can align with an abduction angle feature (e.g., abduction angle feature 111, abduction angle feature 113) disposed on an end (e.g., right end segment 102, left end segment 103) of a crossbar (e.g., crossbar 101) adjacent to the keyhole. If there are multiple abduction angle features 462 disposed on the base 453 of the locking hub 450, each abduction angle feature 462 can be disposed in such a way as to align with multiple abduction angle features disposed on an end segment of the crossbar. Alternatively, if there are multiple abduction angle features 462 disposed on the base 453 of the locking hub 450, the abduction angle features 462 can be aligned with a single set of abduction angle features disposed on an end segment of the crossbar.

As mentioned above, the locking hub 450 mechanically couples to an end (e.g., right end segment 102, left end segment 103) of the crossbar using one or more coupling features 462. Specifically, one or more abduction angle features 462 of the base 453 of the locking hub 450 can be mechanically coupled to one or more abduction angle features (e.g., abduction angle feature 111, abduction angle feature 113) disposed on an end of a crossbar adjacent to the keyhole. The abduction angle feature 462 of the locking hub 450 can directly couple to an abduction angle feature disposed on an end segment of the crossbar, using one or more of a number of coupling methods, including but not limited to mating threads, compression fittings, tabs, slots, and detents. Alternatively, an abduction angle feature 462 of the locking hub 450 can be indirectly coupled to an abduction angle feature disposed on an end segment of the crossbar, as with the use, for example, of one or more of a number of fastening devices (e.g., a bolt, a screw, a nut, hinge pin, rivet). An example of this latter case is shown below with respect to FIGS. 5A-5C.

In any case, when the abduction angle feature 462 of the locking hub 450 aligns with and couples to an abduction angle feature disposed on an end of a crossbar, an abduction angle of the footplate (and, thus, the foot restraint, described below with respect to FIGS. 14A-16) is set. The intermediate section 452 and the coupling feature 451 are held in a fixed position when the locking hub 450 is coupled to an end of a crossbar using the abduction angle feature 462 of the locking hub 450. In certain example embodiments, each abduction angle feature 462 is recessed so that a fastening device disposed in the abduction angle feature 462 is not damaged or otherwise compromised by normal use (e.g., standing, movement) of the example brace by a user.

Different fixed abduction angles can be achieved using the abduction angle feature 462 of the locking hub 450 and the abduction angle features disposed on an end of a crossbar. For example, if the abduction angle feature 462 is aligned with and coupled to (with or without a fastening device) the abduction angle feature 113, then the abduction angle 197 of the footplate (and, thus, the foot restraint) can be approximately 45°. As another example, if the abduction angle feature 462 is aligned with and coupled to (with or without a fastening device) the abduction angle feature 111, then the abduction angle 198 of the footplate (and, thus, the foot restraint) can be approximately 65°.

The bottom surface 468 of the base 453 of the locking hub 450 can be substantially planar. In certain example embodiments, a number of relief areas 491 are disposed between the bottom surfaces 468 to add strength to the locking hub 450. The height of the base 453 (corresponding to the height of the side wall 466) can be no greater than the height of the side 125 of the end adjacent to where the locking hub 450 is positioned when coupled to the end. In such a case, the locking hub 450 is raised above the level formed by the bottom border 132 of the end.

FIGS. 5A-5C show various views of a subassembly 569 of an example brace in accordance with certain example embodiments. Specifically, FIGS. 5A-5C show the locking hub 450 of FIGS. 4A-4E being disposed within the keyhole 520 (hidden from view) before the locking hub 450 is coupled to the left end segment 503. FIG. 5A shows a top view of the subassembly 569, FIG. 5B shows a bottom view of the subassembly 569, and FIG. 5C shows a side view of the subassembly 569. The left end segment 503 and the central portion (including the top 540 and the back side 541) are substantially the same as the left end segment 103 and the central portion 138 of FIGS. 1A-1D.

Referring to FIGS. 1A-5C, to mechanically couple the locking hub 450 to the left end segment 503, the coupling feature 451 of the locking hub 450 is initially inserted into and raised through the keyhole 520. Specifically, the tab 454 can be raised through the extended section 522 of the keyhole 520, while the remainder of the coupling feature 451 (in this case, the slotted tongue 457, the stop 455, the ramp 456) is raised through the core section 524 of the keyhole 520. Alternatively, such as when the extended section 522 includes the lip 527, the coupling feature 451 and the intermediate section 452 can be inserted into the keyhole 520 at an angle, leading with the tab 454.

In certain example embodiments, the shape of the tab 454 (e.g., rectangular, triangular) from a top view is substantially the same as, or different than, the shape of the extended section 522 of the keyhole 520 of an end (in this case, left end segment 503) of a crossbar. Similarly, the size of the tab 454 from a top view from any particular dimension (across, top to bottom) is less than the size of the extended section 522 of the keyhole 520 in a corresponding dimension. Alternatively, the extended section 522 of the keyhole 520 can be shorter than tab 454. In such a case, the tab 454 (and, thus, the locking hub 450) can be inserted through the extended section 522 (and, thus, the keyhole 520) at an angle.

The coupling feature 451 can be raised until the top surface 465 of the base 453 abuts against the bottom side 507 of the left end segment 503. For example, the coupling feature 451 can be raised until the coupling features 462 of the locking hub 450 abut against one of the sets of abduction angle features (e.g., abduction angle feature 511, abduction angle feature 513) of the left end segment 503. In such a case, the intermediate section 452 of the locking hub 450 is disposed within the core section 524 of the keyhole 520.

When the intermediate section 452 of the locking hub 450 is disposed within the core section 524 of the keyhole 520, then the coupling feature 451 sits above the top 526 of the left end segment 503. Further, because the intermediate section 452 and the core section 524 have substantially the same shape (in this case, cylindrical) and size (e.g., height), with the outer perimeter of the intermediate section 452 being slightly smaller than the inner perimeter of the core section 524, the locking hub 450 can rotate when disposed within the core section 524. Rotating the locking hub 450 when the intermediate section 452 is disposed within the core section 524 is important to set the proper abduction angle, as described below with respect to FIGS. 6A-7B.

In certain example embodiments, one or more features can be disposed on the top surface of the an end (in this case, left end segment 503) to control the rotational movement of the locking hub 450 when the locking hub 450 is disposed within the core section 524 of the keyhole 520. For example, a protrusion (not shown) can extend upward from the top 526 of the left end segment 503 where the recessed area 530 transitions to the top 540 of the central portion of the crossbar. In such a case, the protrusion can act as a stop against the tab 454 to prevent the locking hub 450 from rotating to a certain position or beyond a certain point.

FIGS. 6A and 6B show a top view and a bottom view, respectively, of the subassembly 670 of FIGS. 5A-5C where the locking hub 450 forms a first abduction angle 697 in accordance with certain example embodiments. As shown in FIGS. 6A and 6B, the locking hub 450 of FIGS. 5A-5C is rotated until the tab 454 is positioned within the vertical boundary of the recessed area 530. In such a case, one or more abduction angle features 462 of the locking hub 450 can be aligned with one of at least one set of abduction angle features 511 disposed in the left end segment 503. In this example, each of the two abduction angle features 462 of the locking hub 450 is aligned with the abduction angle feature 511 for each set of abduction angle features disposed in the left end segment 503. In this case, a coupling device 609 (e.g., a bolt) traverses both an abduction angle feature 462 in the locking hub 450 and a corresponding abduction angle feature 511 in the left end segment 503.

In some cases, one or more other coupling devices (e.g., coupling feature 512, a nut) can be used in conjunction with the coupling device 609. As can be seen in this example, the locking hub 450 rotates approximately 180° once the coupling feature 451 of the locking hub 450 passes through the keyhole 520 of the left end segment 503. When the abduction angle features 462 of the locking hub 450 are aligned with the abduction angle features 511 disposed in the left end segment 503, the tab 454 is positioned toward the left end segment (when looking at the top view, as in FIG. 6A) of the recessed area 530.

The recessed area 530 allows the tab 454 to be depressed, which lowers the stop 455 and allows the footplate (described below) to become decoupled from the locking hub 450. In addition, the recessed area 530 can also limit the rotational movement of the tab 454, which helps align the abduction alignment features 462 with a set of abduction angle features (e.g., abduction angle features 511, abduction angle features 513) of the end (e.g., right end segment 502, left end segment 503) of the crossbar 501. Alternatively, the locking hub 450 can freely rotate 360° within the keyhole 520, but the recessed area 530 is the only space in which the tab 454 can be depressed to release the footplate.

FIGS. 7A and 7B show a top view and a bottom view, respectively, of the subassembly 770 of FIGS. 5A-5C where the locking hub 450 forms a second abduction angle 798 in accordance with certain example embodiments. As shown in FIGS. 7A and 7B, the locking hub 450 of FIGS. 5A-5C is rotated until the tab 454 is positioned within the vertical boundary of the recessed area 530. In such a case, one or more abduction angle features 462 of the locking hub 450 can be aligned with one of at least one set of abduction angle features 513 disposed in the left end segment 503. In this example, each of the two abduction angle features 462 of the locking hub 450 is aligned with the abduction angle feature 513 for each set of abduction angle features disposed in the left end segment 503. In this case, a coupling device 609 traverses both an abduction angle feature 462 in the locking hub 450 and a corresponding abduction angle feature 513 in the left end segment 503.

In some cases, one or more other coupling devices (e.g., coupling feature 514, a nut) can be used in conjunction with the coupling device 609. As can be seen in this example, the locking hub 450 rotates approximately 180° once the coupling feature 451 of the locking hub 450 passes through the keyhole 520 of the left end segment 503. When the abduction angle features 462 of the locking hub 450 are aligned with the abduction angle features 513 disposed in the left end segment 503, the tab 454 is positioned toward the right end segment (when looking at the top view, as in FIG. 7A) of the recessed area 530.

FIGS. 8A-8D show various views of another subassembly 872 of the entire (instead of a portion of the) crossbar 501 and both (instead of one) locking hubs 450 from FIGS. 7A and 7B in accordance with certain example embodiments. FIG. 8A shows a top-side perspective view of the subassembly 872. FIG. 8B shows a side view of the subassembly 872. FIG. 8C shows a top view of the subassembly 872. FIG. 8D shows a bottom view of the subassembly 872.

Figure 14A:
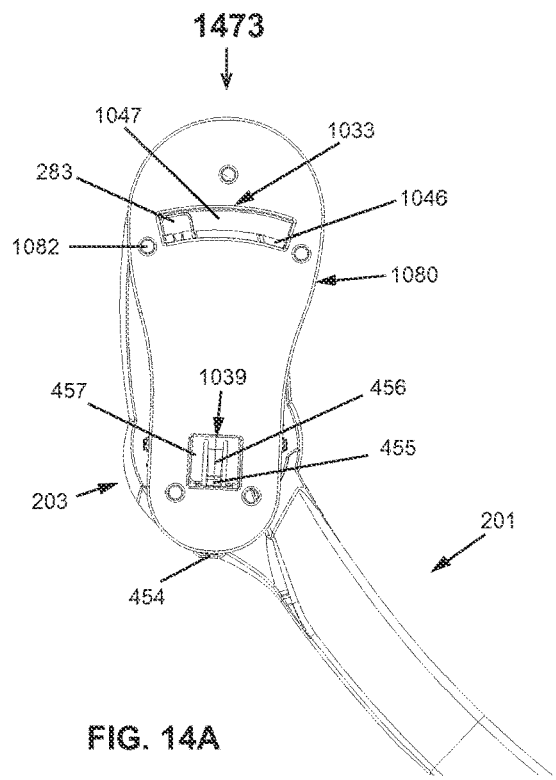
FIGS. 14A and 14B show a top view and a bottom view, respectively, of another crossbar, footplate, and locking hub in accordance with certain example embodiments.

FIGS. 9A-9D show various views of a footplate 980 in accordance with certain example embodiments. FIG. 9A shows a top view of the footplate 980. FIG. 9B shows a rear side view of the footplate 980. FIG. 9C shows a bottom view of the footplate 980. FIG. 9D shows a top perspective view of the footplate 980. Referring to FIGS. 1A-9D, the footplate 980 of FIGS. 9A-9D is substantially flat along the top surface 981, and can have a number of coupling features 982 (in this case, apertures that traverse through the footplate 980) for securing a foot restraint, as shown in FIGS. 14A and 4B above. In addition, or in the alternative, the footplate 980 can include one or more of a number of other coupling features, aside from the apertures, that can be used to mechanically couple the footplate 980 to a foot restraint.

Figure 14B:
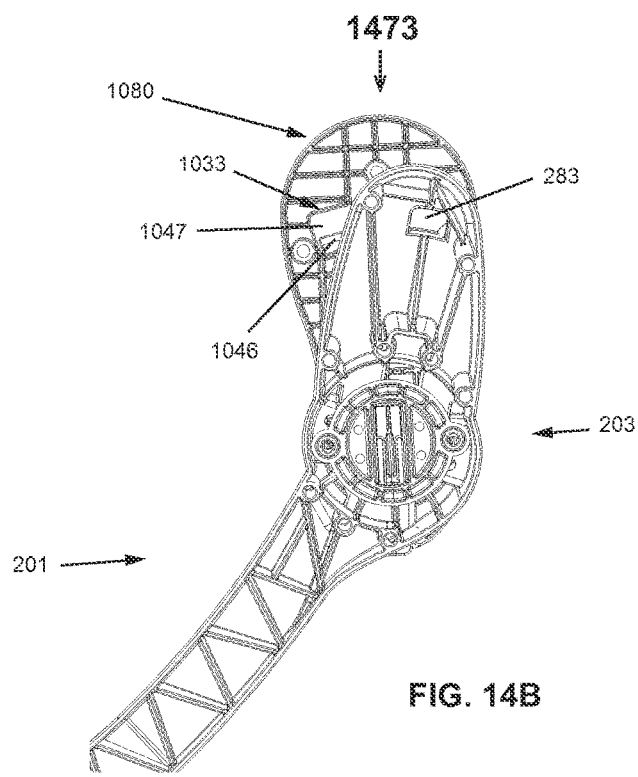

The coupling features 982 can be reinforced on the bottom side by standoffs 993. In such a case, the standoffs 993 can have a height that is less than the height of the reinforcements 949 disposed on the bottom surface 989 of the footplate 980. In such a case, a coupling device (e.g., a rivet, a bolt) can be used to couple the footplate 980 to a foot restraint (as shown in FIGS. 14A and 14B below) without such coupling device extending further away from the bottom surface 989 relative to the reinforcements 949.

In certain example embodiments, the footplate 980 also includes a coupling feature 939 that allows the footplate 980 to couple to a locking hub (e.g., locking hub 450). In this example, the coupling feature 939 includes a slot 988 that starts on the "heel" (back side) of the footplate 980 and is disposed along the bottom surface 989 of the footplate 980, traversing inward toward, but not reaching, the "toe" (front side). The slot 988 can have a bottom portion 983 that is narrower than a top portion 934. The bottom portion 983 can be bounded on one or more sides (in this case, one both sides and the distal end) by a collar 987. The top portion 934 of the slot 988 can have substantially the same length and width as the combination of the collar 987 and the bottom portion 983 of the slot 988. The height of the top portion 934 of the slot 988 can be at least as great as the height of the bottom portion 983 of the slot 988.

The width and height of the top portion 934 can be substantially the same as, or slightly smaller than, the width and height of the slotted tongue 457 of the locking hub 450, which is slidably disposed within the top portion 934 of the slot 988. The width and height of the bottom portion 983 of the slot 988, defined by the collars 987, can be substantially the same as, or slightly smaller than, the width and height of the base 467 of the coupling feature 451 of the locking hub 450.

The coupling feature 939 can also include an aperture 984 that traverses the footplate 980 and is positioned adjacent to the slot 988. The aperture 984 can be defined by one or more sides (e.g., distal side 945, proximal side 986) and can be rectangular in shape so that its edges are parallel to the sides of the slot 988. In this case, the aperture 984 is wider than the bottom portion 983 of the slot 988, as the collars 987 are visible on either side of the aperture 984 in the top view of FIG. 9A. In certain example embodiments, the width of the aperture 984 is at least as great as the width of the ramp 456 and the stop 455 of the locking hub 450.

As shown in FIG. 15 below, the locking hub 450 and the footplate 980 become slidably and detachably coupled to each other by sliding the coupling feature 451 of the locking hub 450 into the slot 988 of the coupling feature 939 of the footplate 980, starting at the heel end. As the ramp 456 slidably enters the slot 988, the bottom surface 948 of the footplate 980 applies a downward force on the ramp 456, causing the ramp 456 (and so also the stop 455) to become substantially planar with the slotted tongue 456 of the coupling feature 451 of the locking hub 450. As the locking hub 450 continues to slide further into the slot 988, the downward force continues to be applied to the ramp 456 by the bottom surface 948 of the footplate 980.

When the locking hub 450 continues to slide within the slot 988 to the point where the stop 455 reaches the proximal side 986 of the aperture 984, the bottom surface 948 of the footplate 980 ends and can no longer force the ramp 456 and the stop 455 downward. At this point, when the stop 455 is in the vertical space of the aperture 984, the ramp 456 returns to its natural position, causing the stop 455 to be located above the proximal side 986 of the aperture 984. As a result, while the locking hub 450 may be able to continue sliding forward within the slot 988 (depending on the length of the slot 988 relative to the length of the slotted tongue 457), if an opposite force is applied to the locking hub 450 to move the locking hub 450 out of the slot 988, the locking hub 450 cannot move beyond the point where the stop 455 abuts against the proximal side 986 that defines the aperture 984.

In certain example embodiments, the length of the slot 988 relative to the length of the slotted tongue 457 is such that the locking hub 450 can only move further into the slot 988, if at all, a slight distance once the stop 455 clears the proximal side 986 and the ramp 456 resumes its default position. In this manner, the coupling feature 939 of the footplate 980 can allow the coupling feature 451 of the locking hub 450 to slide therein and, once the coupling feature 451 has slid far enough into the coupling feature 939 for the stop 455 to engage the proximal side 986, securely couple the locking hub 450 and the footplate 980 together. The thickness of the footplate 980 (between the top surface 981 and the bottom surface 948) can be no greater than the distance that the stop 455 extends into the aperture 984.

To decouple the locking hub 450 and the footplate 980, as shown in FIG. 15 below, the tab 454 of the locking hub 450 can be depressed and, while the tab 454 remains depressed, the footplate 980 can be slid forward, at least far enough that the stop 454 is clear of the proximal side 986 of the coupling feature 939 and abuts against the bottom surface 948 of the footplate 980. In such a case, the tab 454 must be depressed far enough to allow the height (vertical reach) of the stop 455 to decrease to a level that is less than (below) the level of the bottom surface 948 of the footplate 980. The tab 454 can be depressed downward to the extent needed because of the recessed area 530, into which the tab 454 is depressed.

As can be seen in FIGS. 10A-12, the size of the footplate can vary. The footplate 1080 of FIGS. 10A and 10B is larger than the footplate 980 of FIGS. 9A-9D. The footplate 1180 of FIG. 11 is larger than the footplate 980 of FIGS. 9A-9D and the footplate 1080 of FIGS. 10A and 10B, but is smaller than the footplate 1280 of FIG. 12. In certain example embodiments, the width of the various footplates are substantially the same. In addition, the size, shape, and/or configuration of the coupling feature (e.g., coupling feature 939, coupling feature 1239) of the various footplates are substantially the same from one size footplate to another size footplate. This means that the same locking hub 450 can be used with footplates of varying sizes. Further, the size, shape, and/or configuration of the coupling features (e.g., coupling features 1182, coupling features 982) of the various footplates can be substantially the same from one size footplate to another size footplate.

When the footplate exceeds a certain size, the footplate can include one or more additional coupling features that allows for additional support to secure the larger sized footplate to the rest of the example brace. For example, the footplates shown in FIGS. 10A-12 include a coupling feature (coupling feature 1033 in FIGS. 10A and 10B, coupling feature 1133 in FIG. 11, and coupling feature 1233 in FIG. 12). For purposes of describing the features of the footplates of FIGS. 10A-12, footplate 1080 of FIGS. 10A and 10B shall be used for illustrative purposes. However, it should be appreciated that the same description can apply to the footplate 1180 of FIG. 11 and/or the footplate 1280 of FIG. 12.

This coupling feature 1033 in this case includes a slot 1047 that traverses a portion of the width of the footplate 1080 and a lip 1046 disposed along an edge (in this case, the bottom edge) of the slot 1047. The lip 1046 can be positioned at some vertical location (e.g., substantially even with the distal end segment of the reinforcements 1049 extending downward from the bottom surface 1089 of the footplate 1080) to complement the coupling feature (e.g., coupling feature 283) of the end segment of the crossbar.

The slot 1047 in the footplate 1080 can allow the coupling feature (e.g., coupling feature 283) of the end segment of the crossbar to be engaged in the slot 1047 as the stop 455 of the coupling feature 451 of the locking hub 450 is disposed within the aperture 1084 of the footplate 1080. The width of the slot 1047 is designed to allow the coupling feature 1033 in the footplate 1080 to couple to the coupling feature (e.g., coupling feature 283) of the end segment of the crossbar regardless of the abduction angle (the position of the locking hub 450 relative to the end segment of the crossbar). In other words, the coupling feature of the end segment of the crossbar slides within and remains engaged with the slot 1047 in the footplate 1080 regardless of which set of abduction angle features in the end (e.g., right end segment 202, left end segment 203) of the crossbar (e.g., crossbar 201) is aligned with and mechanically coupled to the abduction angle features 462 of the locking hub 450.

The shape, size, and position on the footplate relative to the coupling feature (e.g., coupling feature 1039) is substantially the same between footplate 1080, footplate 1180, and footplate 1280. The coupling feature (e.g., coupling feature 1033 in FIGS. 10A and 10B) can be positioned on the respective footplate in such a way as to complement a coupling feature of the locking hub 450 and/or an end (e.g., right end segment 202, left end segment 203) of the crossbar 501. In this particular example, the coupling feature (e.g., coupling feature 1133 in FIG. 11) can have a size, shape, and location on the footplate that coincides with the coupling feature 283 disposed toward the distal end on end (e.g., right end segment 202, left end segment 203) of the crossbar 201.

Figure 13A:
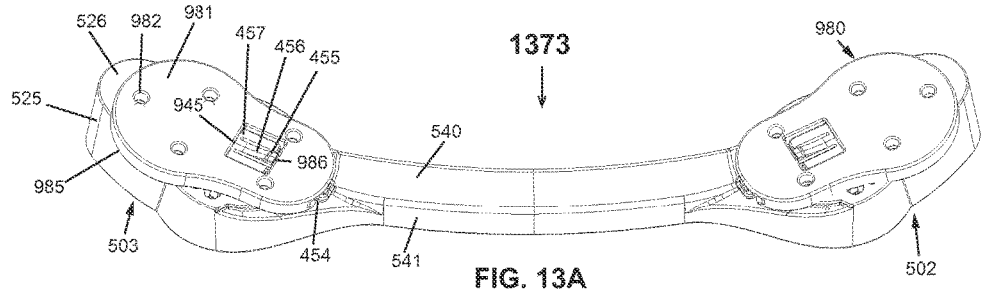
FIGS. 13A-13D show various views of a subassembly of a portion of a crossbar, a footplate, and a locking hub in accordance with certain example embodiments.
Figure 13B:
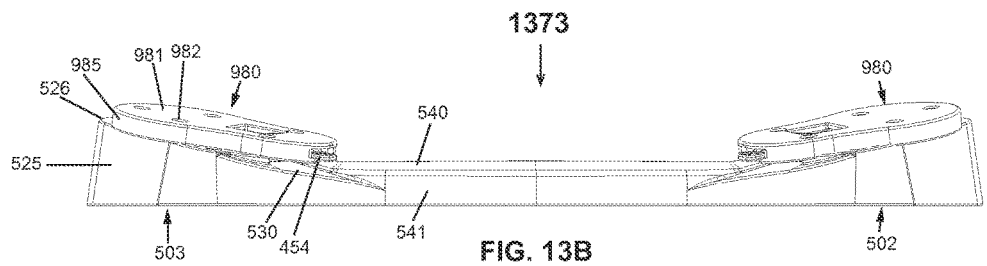
Figure 13C:
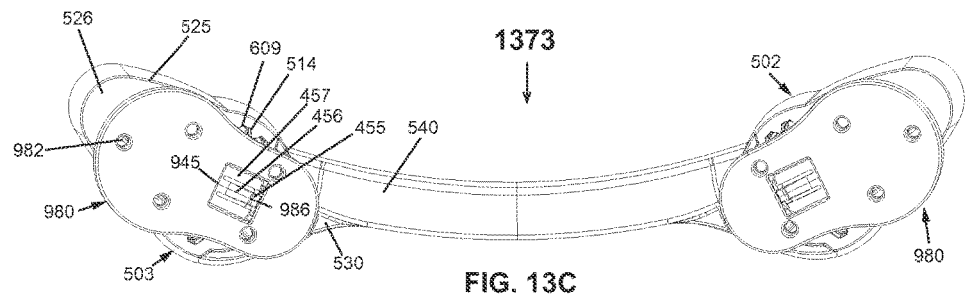
Figure 13D:
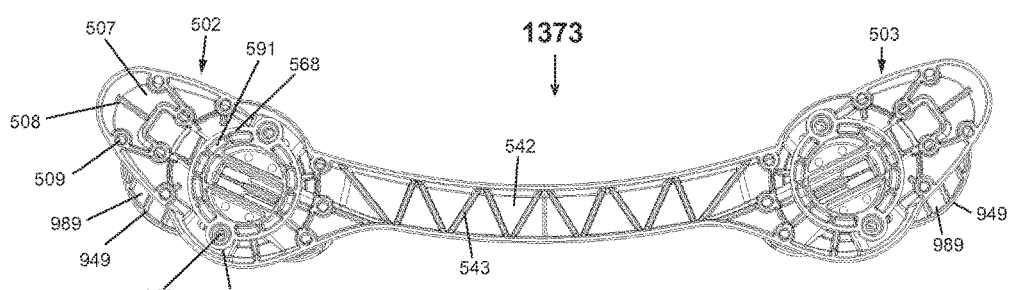

FIGS. 13A-13D show various views of a subassembly 1373 of the brace that includes the subassembly of FIGS. 7A and 7B and the footplate 980 of FIGS. 9A-9D in accordance of certain example embodiments. Specifically, FIG. 13A shows a top-side perspective view of the subassembly 1373. FIG. 13B shows a side view of the subassembly 1373. FIG. 13C shows a top view of the subassembly 1373. FIG. 13D shows a bottom view of the subassembly 1373. Referring to FIGS. 1A-13D, the tab 454 of the locking hub 450 can have any length. In other words, the tab 454 can extend laterally beyond (when viewed from above) the footplate 980 when the footplate 980 is mechanically coupled to the locking hub 450, making the tab 454 easily accessible and, thus, making it easier for a user to decouple the footplate 980 from the locking hub 454.

Conversely, as shown in FIGS. 13A-13D, the tab 454 can be shorter and not extend laterally beyond (when viewed from above) the footplate 980 when the footplate 980 is mechanically coupled to the locking hub 450, making the tab 454 more difficult to access and, thus, making it more difficult for a user to decouple the footplate 980 from the locking hub 450. In other words, when the tab 454 is shorter and does not extend laterally beyond (when viewed from above) the footplate 980 when the footplate 980 is mechanically coupled to the locking hub 450, a deliberate action must be performed to depress the tab 454, which in turn puts the stop 456 in a depressed position and so releases the stop 456 from the proximal side 986 of the aperture 984. If the footplate 980 is moved forward away from the central portion 538 while the tab 454 (and so the stop 456) is in the depressed position, the footplate 980 becomes decoupled from the end (e.g., left end segment 502, right end segment 502) of the crossbar.

FIGS. 14A and 14B show a top view and a bottom view, respectively, of another subassembly 1473 having the crossbar 201 of FIGS. 2A-2D, the footplate 1080 of FIGS. 10A and 10B, and the locking hub 450 of FIGS. 4A-4E in accordance with certain example embodiments. The subassembly 1473 of FIGS. 14A and 14B is substantially the same as the subassembly 1373 of FIGS. 13A-13D, except that subassembly 1473 includes the coupling feature 1033 of the footplate 1080 and the coupling feature 283 of the end (in this case, the left end segment 203) of the crossbar 201. As shown in FIGS. 14A and 14B, and as described above, the width of the slot 1047 is designed to allow the coupling feature 1033 in the footplate 1080 to couple to the coupling feature 283 of the left end segment 203 of the crossbar 201 regardless of the abduction angle (the position of the locking hub 450 relative to the left end segment 203 of the crossbar 201). In other words, the coupling feature 283 of the left end segment 203 of the crossbar 201 slides within and remains engaged with the slot 1047 in the footplate 1080 regardless of which set of abduction angle features in the left end segment 203 of the crossbar 201 is aligned with and mechanically coupled to the abduction angle features 462 of the locking hub 450.

Figure 15A:
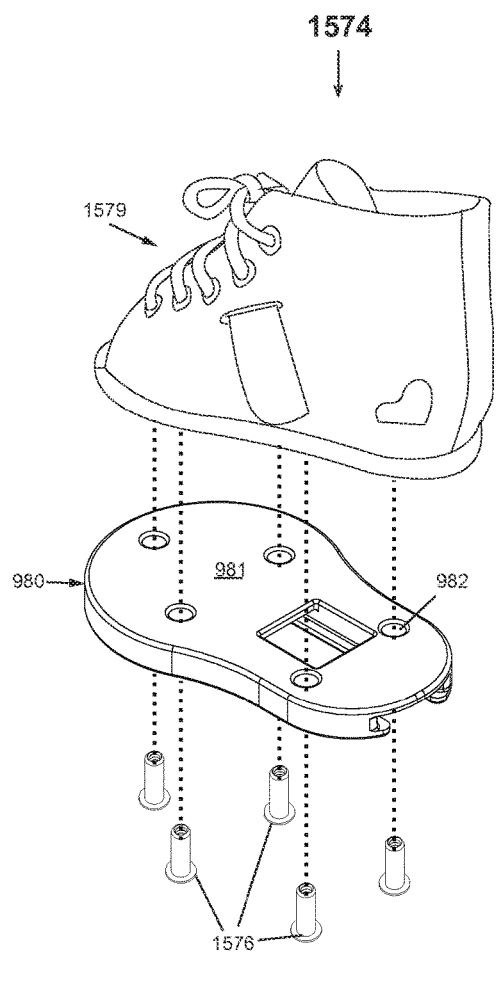
FIGS. 15A and 15B show various exploded views of a subassembly of a footplate and a shoe in accordance with certain example embodiments.
Figure 15B:
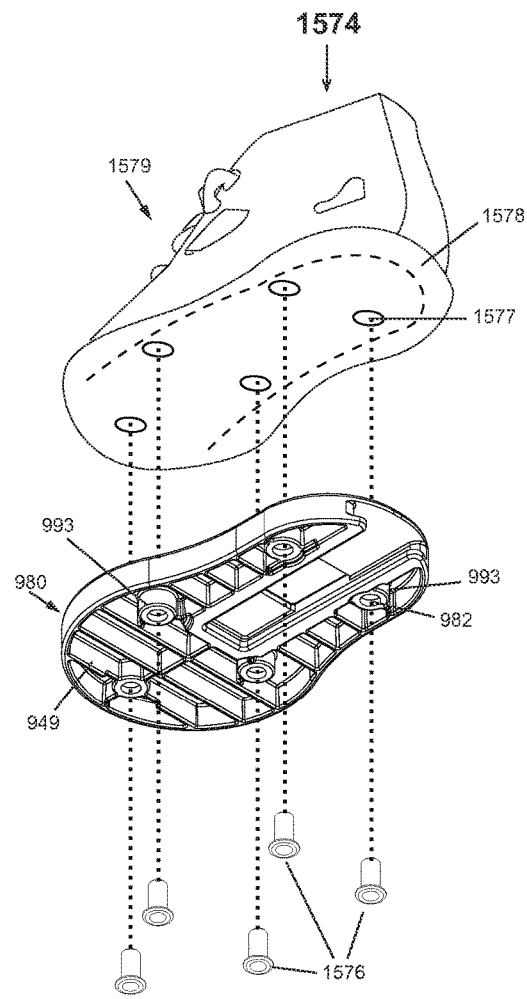

FIGS. 15A and 15B show a top-side perspective view and a bottom-side perspective view, respectively, of a subassembly 1574 of an example brace in accordance of certain example embodiments. The subassembly 1574 in this case include a foot restraint 1579, the footplate 980 of FIGS. 9A-9D, and a number of optional coupling devices 1576. The example foot restraint 1579 includes a number of coupling features 1577 disposed on the bottom surface 1578. The foot restraint 1579 can be made of one or more of a number of materials, including but not limited to a flexible fabric, plastic, metal, rubber, leather, and cork. The coupling features 1577 can be of any shape, size, and configuration sufficient to complement the coupling features 982 of the footplate 980.

The coupling features 1577 of the foot restraint 1579 and the coupling features 982 of the footplate 980 can be coupled to each other directly or indirectly. In this example, the coupling features 1577 of the foot restraint 1579 and the coupling features 982 of the footplate 980 are indirectly coupled to each other using the coupling devices 1576. The coupling devices 1576 can have one or more of a number of configurations, including but not limited to a nut, a rivet (as in this case), a clip, and a screw, Each coupling device 1576 in this case is inserted through the bottom of the coupling feature 982 of the footplate 980 and then into the coupling features 1577 of the foot restraint 1579.

Figure 16:
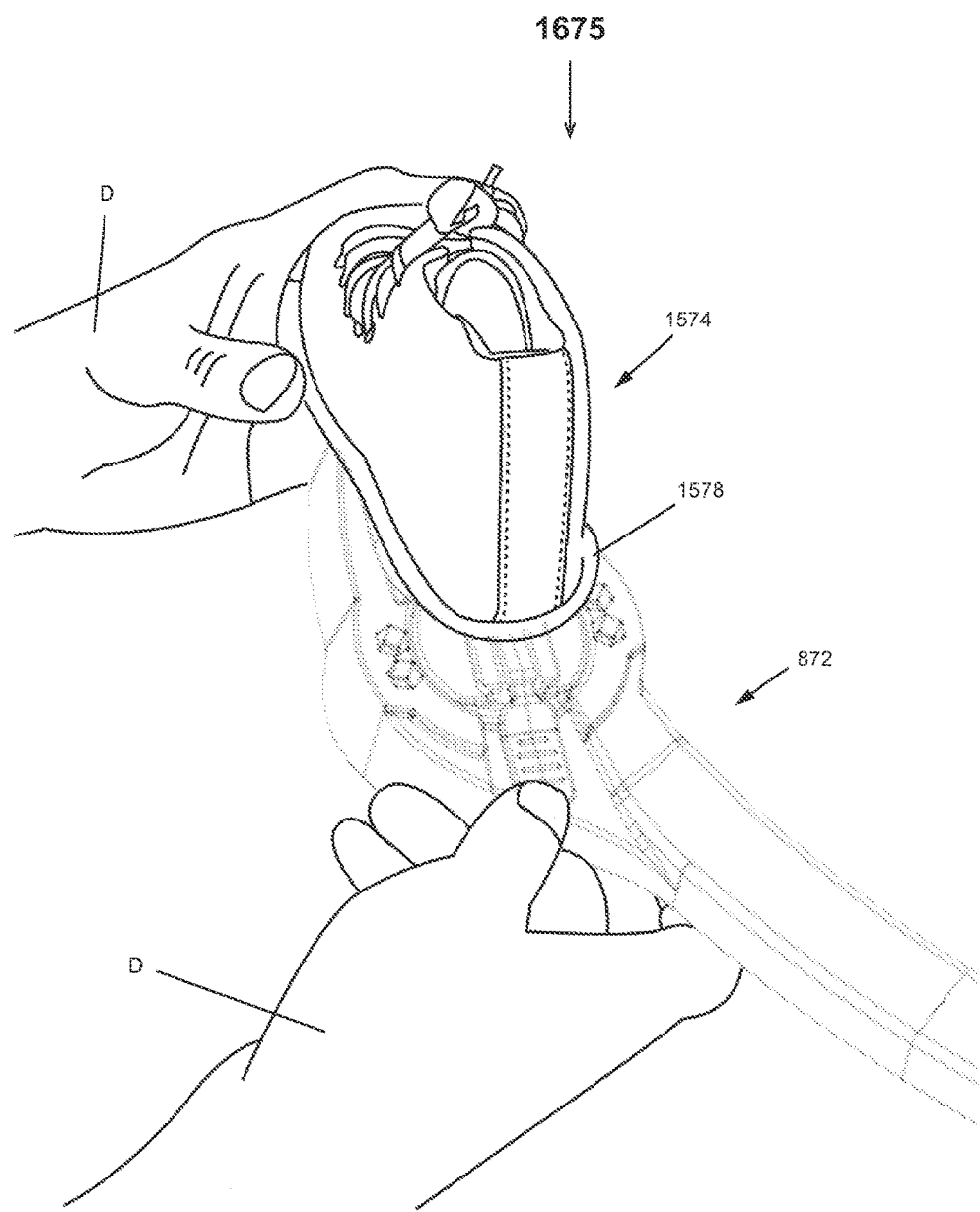
FIG. 16 shows a subassembly of a portion of a crossbar, a footplate, a foot restraint, and a locking hub in accordance with certain example embodiments.

FIG. 16 shows a subassembly 1675 that includes the subassembly 872 of FIGS. 8A-8D and the subassembly 1574 of FIGS. 15A and 15B in accordance with certain example embodiments. As described above, the subassembly 1574 of the foot restraint and the footplate can be decoupled from the locking hub of the subassembly 872. To do so in this case, the tab of the locking hub can be depressed to put the stop in a depressed state. Once this is done, and while the stop continues to be in the depressed state, the subassembly 1574 can be slid outward, toward the distal end segment of the end segment of the crossbar. A user D can perform these actions to couple and decouple the subassembly 1574 and the subassembly 872.

Figure 17:
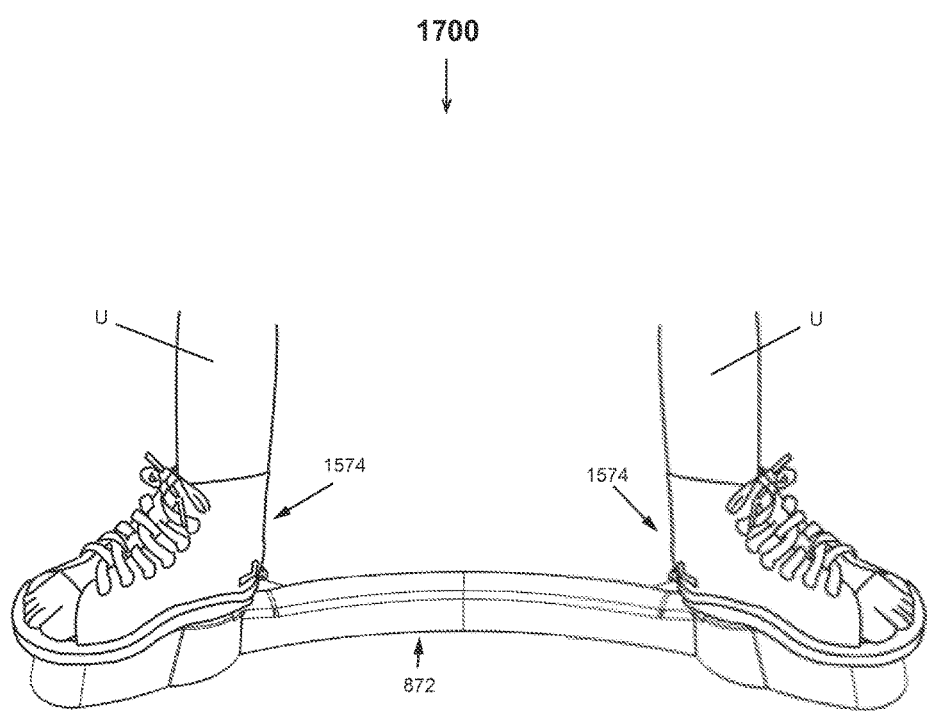
FIG. 17 shows a brace worn by a user in accordance with certain example embodiments.

FIG. 17 shows an example foot abduction brace 1700 worn by a user U. Referring to FIGS. 1A-16, the brace 1700 includes the subassembly 872 of FIGS. 8A-8D coupled to two subassemblies 1574 of FIGS. 15A and 15B. As can be seen, the feet of the user U are positioned at an abduction angle (e.g., abduction angle 198) and a dorsiflexion angle (e.g., dorsiflexion angle 199). In addition, the user U can wear the foot abduction brace 1700 and stand balanced (assuming the surface on which the user U is standing is substantially flat) and/or "walk". In other words, the user U can stand upright while using the foot abduction brace 1700 and, by shifting weight from one side to another, move in a shuffling/walking motion.

Example foot abduction braces can be easy for a doctor (or other similar user) to assemble and set. In addition, example foot abduction braces can be relatively inexpensive to manufacture and distribute because of the materials used, making the braces more accessible to people in developing countries and in otherwise impoverished areas. Example foot abduction braces can be durable and effective for treating the condition causing the foot abduction. Further, example foot abduction braces can be difficult for a user to adjust without proper tools. Example foot abduction braces can be relatively lightweight. Further, example foot abduction braces can allow a user to stand and move while wearing the brace.

Accordingly, many modifications and other embodiments set forth herein will come to mind to one skilled in the art to which foot abduction braces pertain having the benefit of the teachings presented in the foregoing descriptions and the associated drawings. Therefore, it is to be understood that foot abduction braces are not to be limited to the specific embodiments disclosed and that modifications and other embodiments are intended to be included within the scope of this application. Although specific terms are employed herein, they are used in a generic and descriptive sense only and not for purposes of limitation.

What is claimed is:

1. A foot abduction brace, comprising:
a crossbar comprising a planar bottom end;
a first end disposed on one side of the crossbar, wherein the first end comprises a first keyhole, a top, and the planar bottom end, wherein the first keyhole comprises a core section and an extended section that extends laterally away from the core section, and wherein the top of the first end creates a first dorsiflexion angle with the crossbar;
a first locking hub removably coupled to the first end in a first position of a plurality of positions, wherein the first locking hub is disposed in the core section of the first keyhole and comprises a first coupling feature disposed at a top end of the first locking hub, wherein the first coupling feature comprises a tab;
a first footplate comprising a first complementary coupling feature that removably couples to the first coupling feature of the first locking hub; and
a first foot restraint mechanically coupled to the first footplate,
wherein the first position creates a first abduction angle between the first foot restraint and a position that is perpendicular to a longitudinal axis of the crossbar,
wherein the tab fits within the extended section of the first keyhole when the first locking hub is inserted into or removed from the first keyhole,
wherein the tab is disposed above and extends beyond the keyhole when the locking hub is coupled to the first end.

2. The foot abduction brace of claim 1, wherein the tab is mechanically coupled to a stop of the first coupling feature.

3. The foot abduction brace of claim 2, wherein the first complementary coupling feature comprises a slot and an aperture adjacent to the slot, wherein the aperture is bounded by a proximal side, wherein the first locking hub couples to the footplate when the first coupling feature slides into the slot and the stop protrudes through the aperture.

4. The foot abduction brace of claim 3, wherein the stop is forced into a depressed position when the stop of the first coupling feature is in the slot, and wherein the stop reverts to a normal position when the stop reaches the aperture.

5. The foot abduction brace of claim 4, wherein depressing the tab forces the stop into the depressed position, and wherein sliding the first footplate away from the locking hub when the stop is in the depressed position decouples the first footplate from the first locking hub.

6. The foot abduction brace of claim 2, wherein the first coupling feature is disposed atop an intermediate section, wherein the intermediate section is shaped substantially the same as a core section of the first keyhole and is disposed within the core section of the first keyhole when the first locking hub is mechanically coupled to the first footplate.

7. The foot abduction brace of claim 6, wherein the tab extends laterally beyond a vertical extension of the intermediate section, wherein the stop, a slotted tongue, and a ramp of the first coupling feature are contained within the vertical extension of the intermediate section, and wherein the tab is shaped substantially the same as the extended section of the first keyhole.

8. The foot abduction brace of claim 7, wherein the tab is disposed within a recessed area of the crossbar, wherein the recessed area allows the tab to be depressed, and wherein the recessed area is positioned within the rotational range of motion of the tab.

9. The foot abduction brace of claim 8, wherein the tab does not extend, when viewed from above, beyond the first footplate when the first footplate is mechanically coupled to the first locking hub.

10. The foot abduction brace of claim 8, wherein the recessed area is positioned adjacent to the core section of the first keyhole, and wherein the recessed area is located substantially opposite the extended section of the first keyhole.

11. The foot abduction brace of claim 2, wherein the at least one locking hub further comprises a base, wherein the base comprises at least one abduction angle feature, wherein the at least one abduction angle feature couples to at least one set of complementary abduction angle features disposed on the first end adjacent to the at least one keyhole, where the first locking hub is coupled to the first end in the first position when the at least one abduction angle feature is coupled to a first set of the at least one set of complementary abduction angle features, wherein the abduction angle of the first position is 45°.

12. The foot abduction brace of claim 11, further comprising:
at least one fastening device that couples the at least one abduction angle feature to the at least one set of complementary abduction angle features.

13. The foot abduction brace of claim 11, wherein the at least one abduction angle feature, when coupled to a second set of complimentary abduction angle features, puts the locking hub in a second position, wherein the second position form an abduction angle of 65° relative to a foot position that is perpendicular to a longitudinal axis of the crossbar.

14. The foot abduction brace of claim 1, wherein the crossbar, the first locking hub, and the first footplate is made of plastic.

15. The foot abduction brace of claim 1, wherein the dorsiflexion angle is 10°.

16. The foot abduction brace of claim 1, wherein the first end further comprises a second coupling feature disposed at a distal end segment of the first end, wherein the footplate further comprises a second complementary coupling feature, wherein the second coupling feature and the second complementary coupling feature are movably coupled to each other when the footplate is mechanically coupled to the locking hub.

17. The foot abduction brace of claim 16, wherein the second coupling feature is a tab, and wherein the second complementary coupling feature is a slot.

18. The foot abduction brace of claim 1, further comprising:
a second end disposed on another side of the crossbar, wherein the second end comprises a first keyhole, a top, and the planar bottom end, and wherein the top of the second end creates the first dorsiflexion angle with the crossbar;

a second locking hub removably coupled to the second end in the first position in the plurality of positions, wherein the second locking hub is disposed in the second keyhole and comprises the first coupling feature disposed at a top end of the second locking hub;

a second footplate comprising a first complementary coupling feature that removably couples to the first coupling feature of the second locking hub; and a second foot restraint mechanically coupled to the second footplate.

19. The foot abduction brace of claim 1, wherein the planar bottom end of the crossbar, the first end, and the second end allow a user to stand balanced while feet of the user are positioned in the first foot restraint and the second foot restraint.

* * * * *